US008202996B2

(12) United States Patent
Perrone et al.

(10) Patent No.: US 8,202,996 B2
(45) Date of Patent: Jun. 19, 2012

(54) CRYSTALLINE FORMS OF N-(TERT-BUTOXYCARBONYL)-3-METHYL-L-VALYL-(4R)-4-((7-CHLORO-4-METHOXY-1-ISOQUINOLINYL)OXY)-N-((1R,2S)-1-((CYCLOPROPYLSULFONYL)-CARBAMOYL)-2-VINYLCYCLOPROPYL)-L-PROLINAMIDE

(75) Inventors: Robert Kevin Perrone, Belle Mead, NJ (US); Anne I. Song, Upper Saddle River, NJ (US); Chenchi Wang, Somerset, NJ (US); William Ying, Martinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 728 days.

(21) Appl. No.: 12/329,969

(22) Filed: Dec. 8, 2008

(65) Prior Publication Data

US 2009/0202476 A1    Aug. 13, 2009

Related U.S. Application Data

(60) Provisional application No. 61/015,795, filed on Dec. 21, 2007.

(51) Int. Cl.
*C07D 217/22* (2006.01)
*A61K 31/47* (2006.01)
(52) U.S. Cl. .......................................... 546/142; 514/309
(58) Field of Classification Search .................. None
See application file for complete search history.

(56) References Cited

U.S. PATENT DOCUMENTS

| | | | |
|---|---|---|---|
| 5,223,432 | A | 6/1993 | Wirz et al. |
| 7,449,479 | B2 | 11/2008 | Wang et al. |
| 2005/0153877 | A1 | 7/2005 | Miao et al. |
| 2005/0209135 | A1 | 9/2005 | Busacca et al. |
| 2006/0199773 | A1 | 9/2006 | Sausker et al. |
| 2006/0257980 | A1 | 11/2006 | Li |
| 2007/0078081 | A1 | 4/2007 | Casarez et al. |
| 2008/0032936 | A1 | 2/2008 | Gai et al. |
| 2008/0039375 | A1 | 2/2008 | Moore et al. |
| 2008/0039470 | A1 | 2/2008 | Niu et al. |
| 2008/0181868 | A1 | 7/2008 | Sun et al. |
| 2008/0279821 | A1 | 11/2008 | Niu et al. |

FOREIGN PATENT DOCUMENTS

| | | |
|---|---|---|
| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |

(Continued)

OTHER PUBLICATIONS

U.S. Appl. No. 12/202,603, filed Sep. 2, 2008, Wang et al.

(Continued)

*Primary Examiner* — Janet Andres
*Assistant Examiner* — Heidi Reese
(74) *Attorney, Agent, or Firm* — Pamela A. Mingo

(57) ABSTRACT

The present disclosure generally relates to crystalline forms of N-(tert-butoxycarbonyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide. The present disclosure also generally relates to a pharmaceutical composition comprising one or more of the crystalline forms, as well of methods of using the crystalline forms in the treatment of Hepatitis C virus (HCV) and methods for obtaining such crystalline forms.

12 Claims, 9 Drawing Sheets

FOREIGN PATENT DOCUMENTS

| | | |
|---|---|---|
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/010804 | 1/2009 |
| WO | WO 2009/014730 | 1/2009 |

OTHER PUBLICATIONS

U.S. Appl. No. 12/418,677, filed Apr. 6, 2009, Sin et al.
U.S. Appl. No. 12/464,954, filed May 13, 2009, Sun et al.
U.S. Appl. No. 12/465,142, filed May 13, 2009, Sin et al.
U.S. Appl. No. 12/473,188, filed May 27, 2009, Wang et al.
U.S. Appl. No. 12/473,741, filed May 28, 2009, Wang et al.
Lauer, G.M. et al., "Hepatitis C Virus Infection", The New England Journal of Medicine, vol. 345, No. 1, pp. 41-52 (2001).
Llinás-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).
Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).
Ribeiro, C.M.R. et al., "Ultrasound in enzymatic resolution of ethyl 3-hydroxy-3-phenylpropanoate", Tetrahedron Letters, vol. 42, pp. 6477-6479 (2001).
Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).
Wirz, B. et al., "Enzymatic preparation of homochiral 2-isobutyl succinic acid derivatives", Tetrahedron: Asymmetry, vol. 8, No. 2, pp. 187-189 (1997).
Yang, S., "Chemoenzymatic Synthesis of (R)-(—)-Citramalic Acid", Synthesis, pp. 365-366 (1992).

CRYSTALLINE FORMS OF N-(TERT-BUTOXYCARBONYL)-3-METHYL-L-VALYL-(4R)-4-((7-CHLORO-4-METHOXY-1-ISOQUINOLINYL)OXY)-N-((1R,2S)-1-((CYCLOPROPYLSULFONYL)0-CARBAMOYL)-2-VINYLCYCLOPROPYL)-L-PROLINAMIDE

CROSS-REFERENCE TO RELATED APPLICATIONS

This application claims the benefit of U.S. Provisional Application Ser. No. 61/015,795 filed Dec. 21, 2007.

The present disclosure generally relates to crystalline forms of N-(tert-butoxycarbonyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide. The present disclosure also generally relates to a pharmaceutical composition comprising one or more of the crystalline forms, as well of methods of using the crystalline forms in the treatment of Hepatitis C virus (HCV) and methods for obtaining such crystalline forms.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40 percent of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

The compound N-(tert-butoxycarbonyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide is useful for the treatment of HCV infection. During extensive crystallization studies, two crystalline free acid forms, herein referred to as Form H-1 (hydrate) and Form T1F-1/2 (anhydrous) were isolated. It has been found that each of these forms can be repeatedly crystallized on large scale and that each polymorph possesses characteristics that are acceptable for commercial use.

Compound (I)

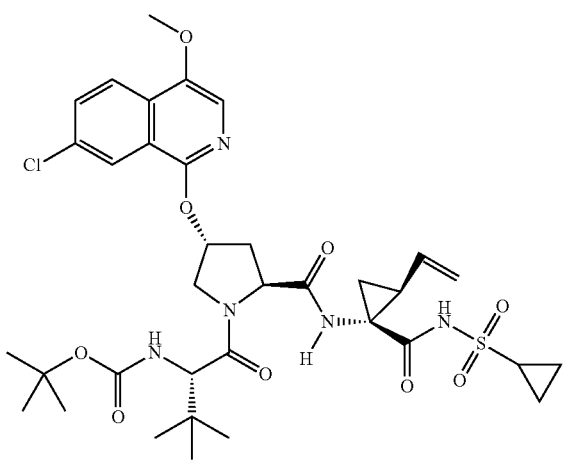

Depending on the humidity, Compound (I) can exist as T1F-1/2 (<15% relative humidity), H-1 (>45% relative humidity), or a mixture of the two at ~15-45% relative humidity. FIG. 1 shows the interconversion of Forms H-1 and T1F-1/2 as a function of relative humidity. In aqueous solutions, Compound (I) exists as H-1, and Form T1F-1/2 rapidly converts to H-1 when suspended in water.

In a first aspect the present disclosure provides Form H-1 of

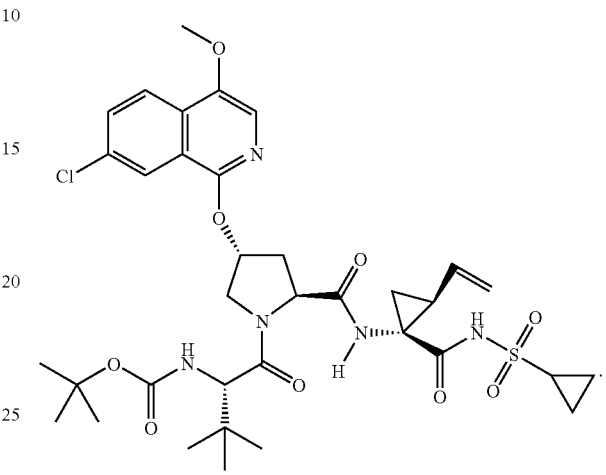

In a second aspect the present disclosure provides Form H-1 of

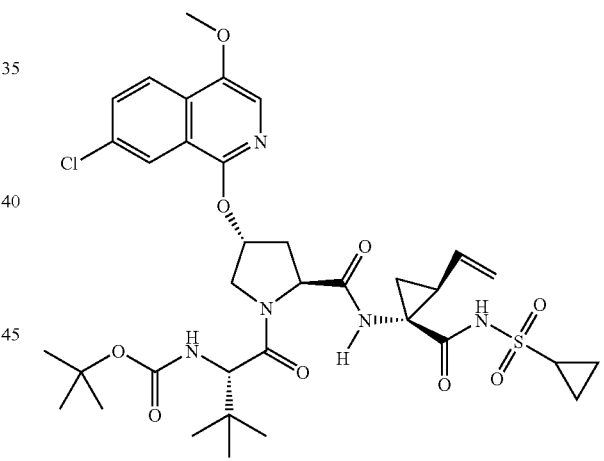

characterized by the following unit cell parameters:

Cell dimensions: a=10.0802 Å b=16.6055 Å c=24.9294 Å

α=90.00 degrees

β=90.00 degrees

γ=90.00 degrees

Space group $P2_1 2_1 2_1$

Molecules/unit cell 4 wherein measurement of said crystalline form is at a temperature between about 20° C. to about 25° C.

In a third aspect the present disclosure provides Form H-1 of

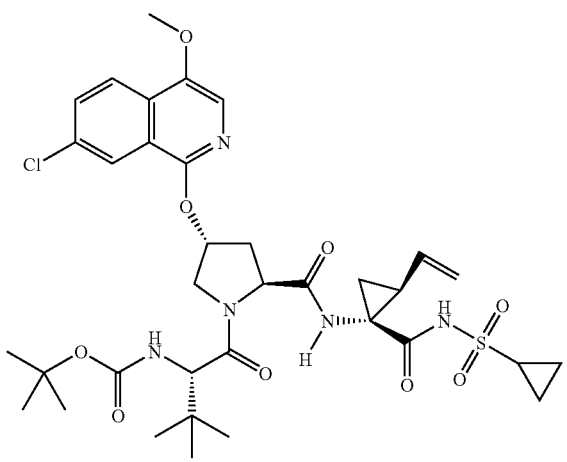

characterized by fractional atomic coordinates within the unit cell as listed in Table 3.

In a fourth aspect the present disclosure provides Form H-1 of

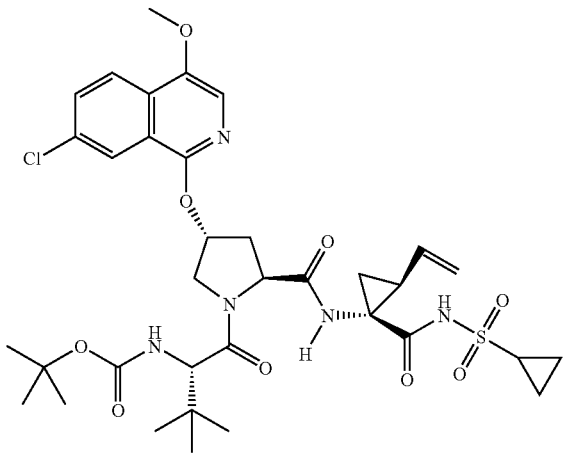

with characteristic peaks in the powder X-Ray diffraction pattern at values of two theta of 6.3±0.1, 7.1±0.1, 9.4±0.1, 10.3±0.1, 12.7±0.1, 13.8±0.1, 17.5±0.1, 18.7±0.1, 20.6±0.1, and 22.5±0.1 at a temperature between about 20° C. and about 25° C.

In a fifth aspect the present disclosure provides Form H-1 of

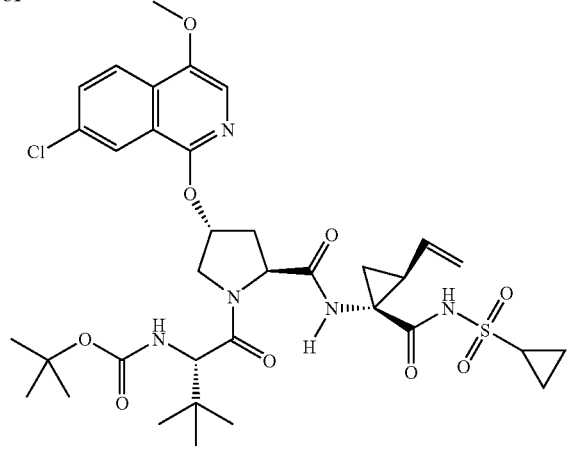

characterized by one or more of the following:

a) a unit cell with parameters substantially equal to the following:
   Cell dimensions: a=10.0802 Å
   b=16.6055 Å
   c=24.9294 Å
   α=90.00 degrees
   β=90.00 degrees
   γ=90.00 degrees
   Space group $P2_12_12_1$
   Molecules/unit cell 4
wherein measurement of said crystalline form is at a temperature between about 20° C. to about 25° C.;

b) characteristic peaks in the powder X-Ray diffraction pattern at values of two theta of 6.3±0.1, 7.1±0.1, 9.4±0.1, 10.3±0.1, 12.7±0.1, 13.8±0.1, 17.5±0.1, 18.7±0.1, 20.6±0.1 and 22.5±0.1 at a temperature between about 20° C. and about 25° C.; and/or c) characterized by fractional atomic coordinates within the unit cell as listed in Table 3.

In a sixth aspect the present disclosure provides substantially pure Form H-1 of

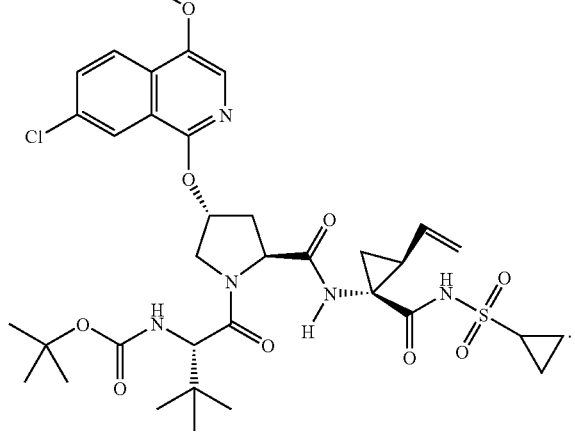

In a first embodiment of the sixth aspect Form H-1 has a purity of at least 95 weight percent. In a second embodiment of the sixth aspect Form H-1 has a purity of at least 99 weight percent.

In a seventh aspect the present disclosure provides Form T1F-1/2 of

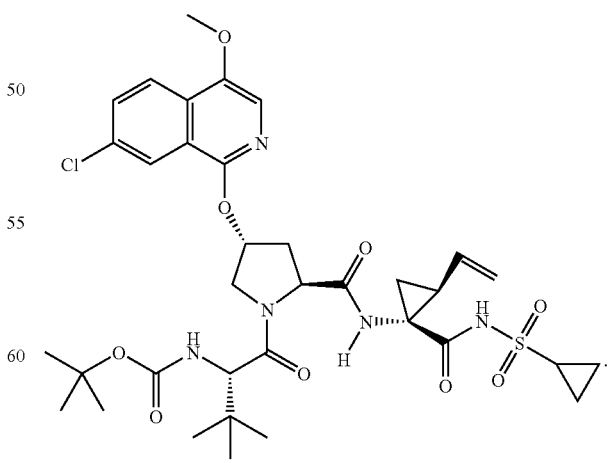

In an eighth aspect the present disclosure provides Form T1F-1/2 of

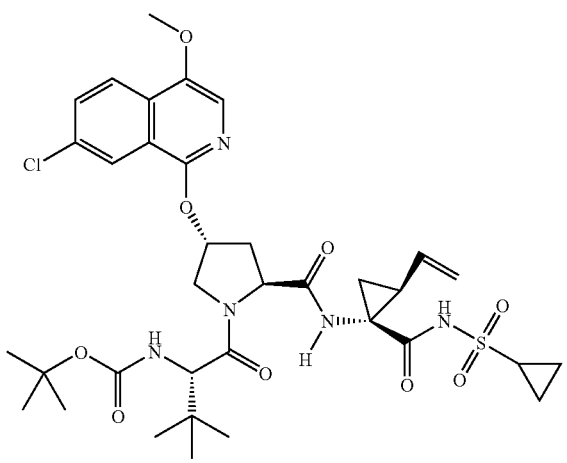

with characteristic peaks in the powder X-Ray diffraction pattern at values of two theta of 7.3±0.1, 9.1±0.1, 10.0±0.1, 10.6±0.1, 11.1±0.1, 12.3±0.1, 15.6±0.1, 20.1±0.1, 20.9±0.1, and 27.8±0.1 at a temperature between about 20° C. and about 25° C.

In a ninth aspect the present disclosure provides Form T1F-1/2 of

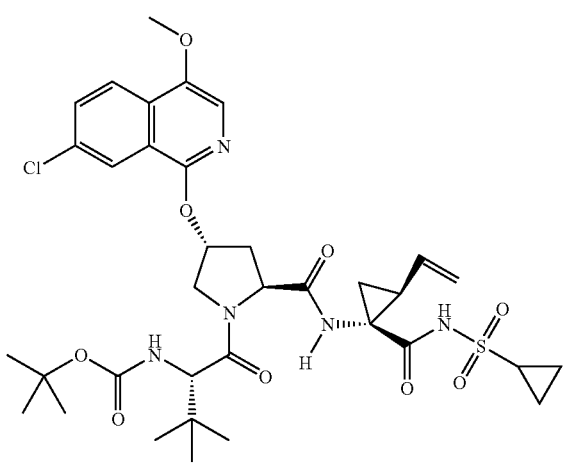

characterized by one or more of the following:

a) characteristic peaks in the powder X-Ray diffraction pattern at values of two theta of 7.3±0.1, 9.1±0.1, 10.0±0.1, 10.6±0.1, 11.1±0.1, 12.3±0.1, 15.6±0.1, 20.1±0.1, 20.9±0.1, and 27.8±0.1 at a temperature between about 20° C. and about 25° C.; and/or c) a first endotherm related to the melt with onset typically in the range of 140-145° C., followed by decomposition.

In a tenth aspect the present disclosure provided substantially pure Form T1F-1/2 of

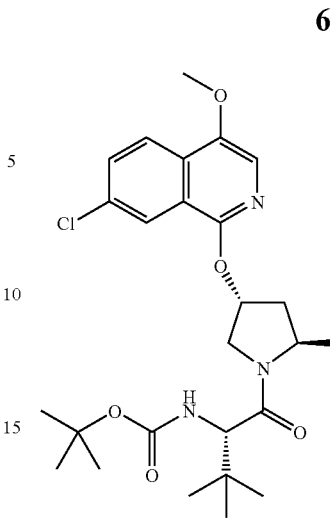

In a first embodiment of the tenth aspect T1F-1/2 has a purity of at least 95 weight percent. In a second embodiment of the tenth aspect Form T1F-1/2 has a purity of at least 99 weight percent.

In an eleventh aspect the present disclosure provides a mixture of Form H-1 and Form T1F-1/2 of

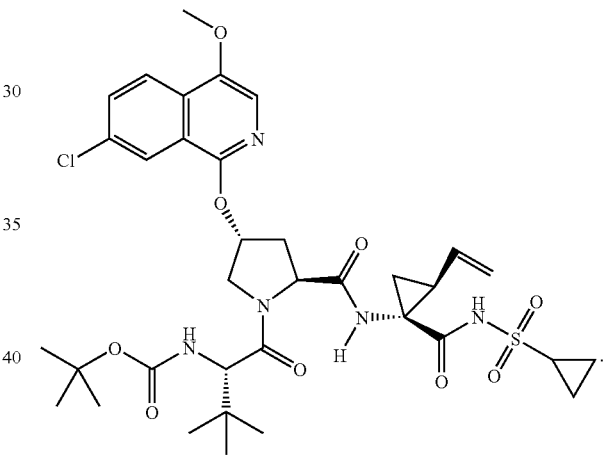

In a twelfth aspect the present disclosure provides a pharmaceutical composition comprising Form H-1, Form T1F-1/2, or a mixture thereof of

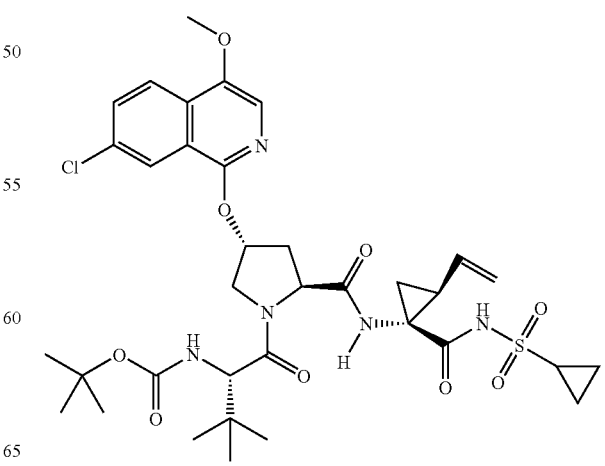

and a pharmaceutically acceptable carrier or diluent.

In a thirteenth aspect the present disclosure provides a pharmaceutical composition comprising Form H-1, Form T1F-1/2, or a mixture thereof of

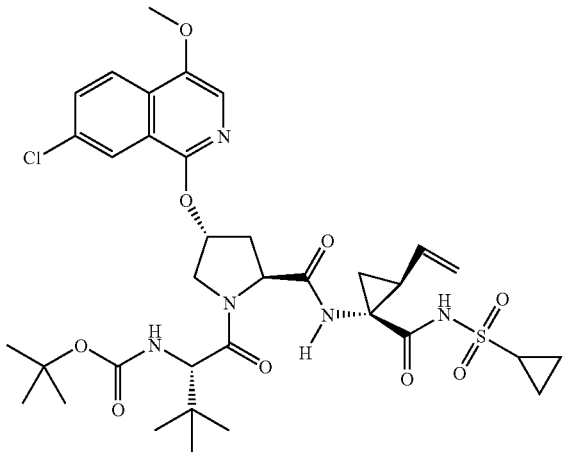

in combination with at least one additional compound having anti-HCV activity. In a first embodiment of the thirteenth aspect at least one of the additional compounds having anti-HCV activity is an interferon or ribavirin. In a second embodiment of the thirteenth aspect the interferon is selected from interferon alpha 2B, pegylated interferon alpha, consensus interferon, interferon alpha 2A, and lymphoblastiod interferon tau.

In a third embodiment of the thirteenth aspect the present disclosure provides a pharmaceutical composition comprising Form H-1, Form T1F-1/2, or a mixture thereof of

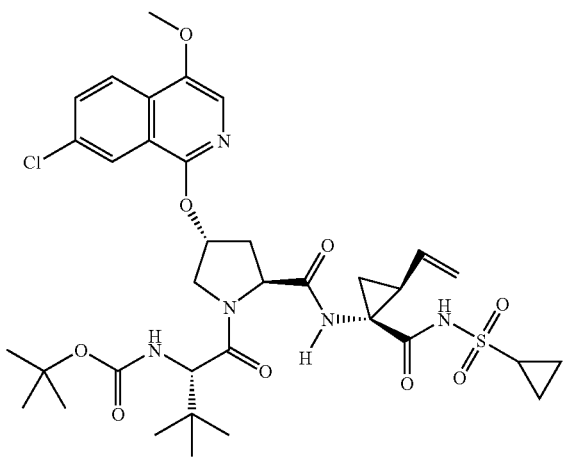

in combination with at least one additional compound having anti-HCV activity wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fourteenth aspect the present disclosure provides a method of treating HCV infection in a mammal comprising administering to the mammal a therapeutically-effective amount of Form H-1, Form T1F-1/2, or a mixture thereof of

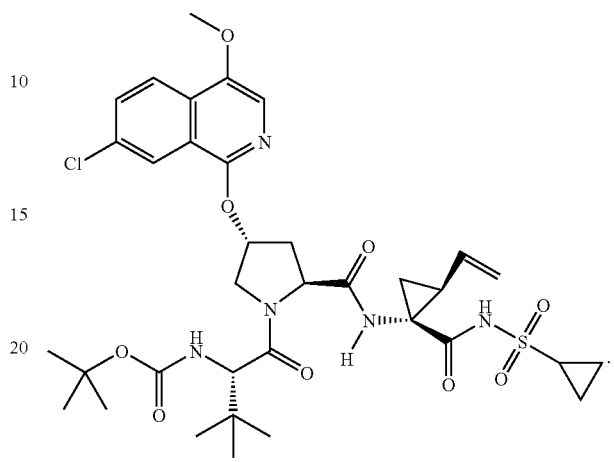

In a first embodiment of the fourteenth aspect the mammal is a human.

Other embodiments of the present disclosure may comprise suitable combinations of two or more of embodiments and/or aspects disclosed herein.

Yet other embodiments and aspects of the disclosure will be apparent according to the description provided below.

The compounds of the present disclosure may also exist as tautomers and rotamers; therefore the present disclosure also encompasses all tautomeric forms and rotamers.

Figure 1:
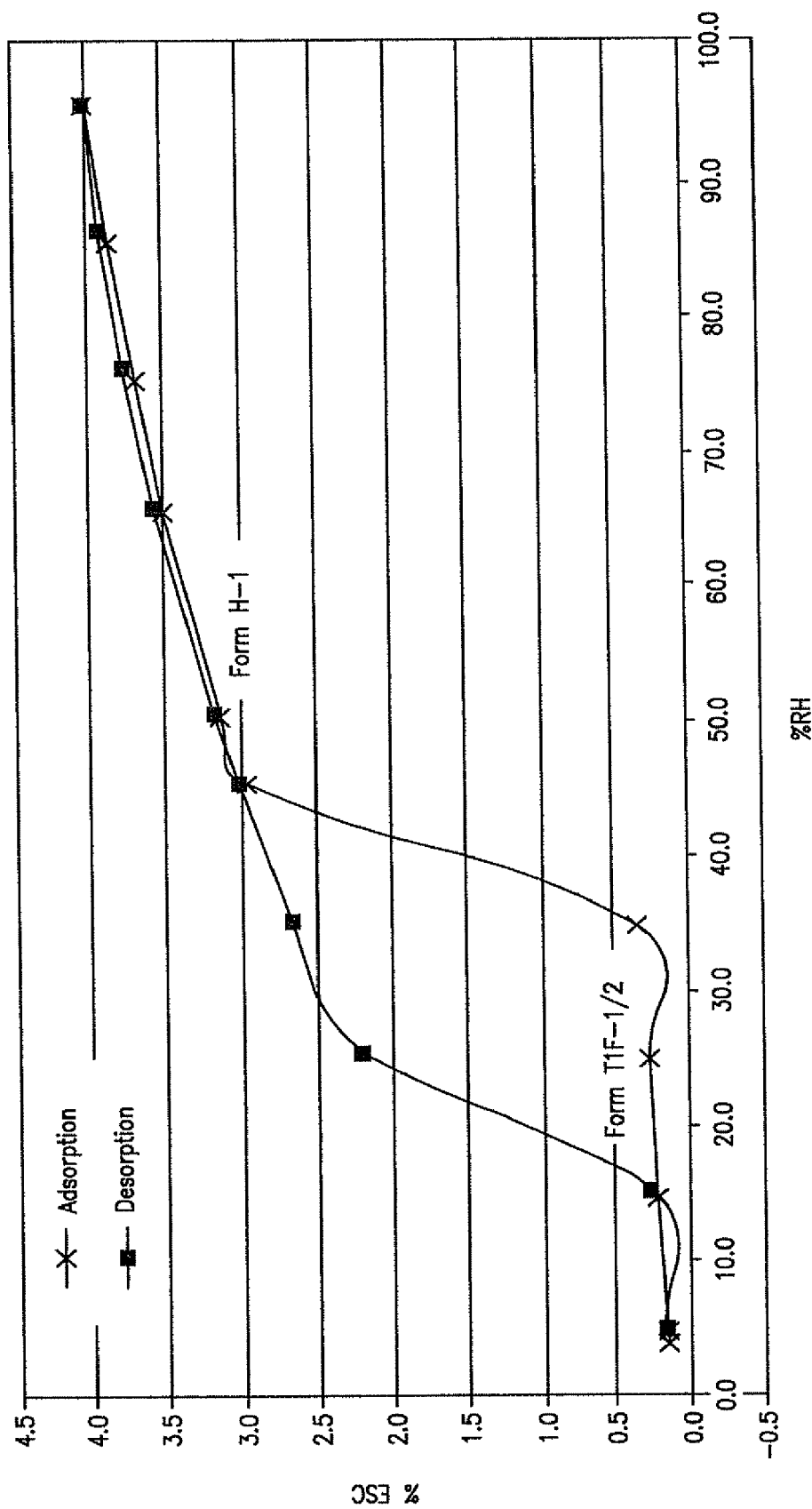
FIG. 1 illustrates the interconversion of Form H-1 and T1F-1/2 as a function of relative humidity.

The disclosure relates to crystalline forms of Compound (I).

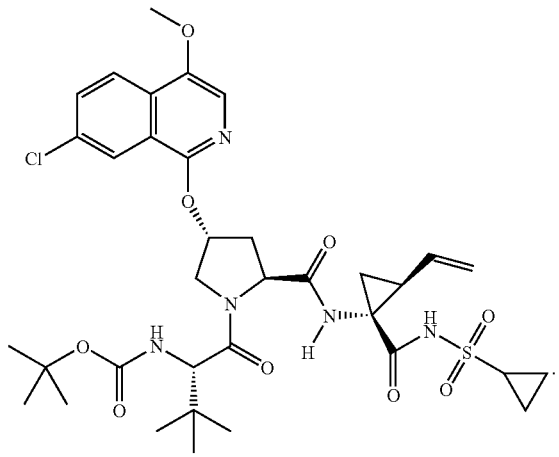

(I)

Definitions

As used herein "polymorph" refers to crystalline forms having the same chemical composition but different spatial arrangements of the molecules, atoms, and/or ions forming the crystal.

The term "pharmaceutically acceptable," as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The term "substantially pure," as used herein refers to either Form H-1 or Form T1F-1/2 of Compound (I) which is great than about 90% pure. This means that the polymorph of Compound (I) does not contain more than about 10% of any other compound, and, in particular, does not contain more than about 10% of any other form of Compound (I).

The term "therapeutically effective amount," as used herein, is intended to include an amount of the crystalline forms of Compound (I) that is effective when administered alone or in combination to treat Hepatitis C. The crystalline forms of Compound (I) and pharmaceutical compositions thereof may be useful in treating Hepatitis C. If Compound (I) is used in combination with another medication, the combination of compounds described herein may result in a synergistic combination. Synergy, as described for example by Chou and Talalay, *Adv. Enzyme Regul.* 1984, 22, 27-55, occurs when the effect of the compounds when administered in combination is greater than the effect of the compounds when administered alone as single agents.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

In one embodiment the disclosure provides crystalline forms of Compound (I). These crystalline forms of Compound (I) may be employed in pharmaceutical compositions which may optionally include one or more other components selected, for example, from the group consisting of excipients, carriers, and one of other active pharmaceutical ingredients active chemical entities of different molecular structure.

In one embodiment the crystalline forms have phase homogeneity indicated by less than 10 percent, in another embodiment the crystalline forms have phase homogeneity indicated by less than 5 percent, and in another embodiment the crystalline forms have phase homogeneity indicated by less than 2 percent of the total peak area in the experimentally measured PXRD pattern arising from the extra peaks that are absent from the simulated PXRD pattern. In another embodiment the crystalline forms have phase homogeneity with less than 1 percent of the total peak area in the experimentally measured PXRD pattern arising from the extra peaks that are absent from the simulated PXRD pattern.

In one embodiment, a composition is provided consisting essentially of the crystalline form H-1 of Compound (I). The composition of this embodiment may comprise at least 90 weight percent of the crystalline form H-1 of Compound (I), based on the weight of Compound (I) in the composition. The remaining material comprises other form(s) of the compound and/or reaction impurities and/or processing impurities arising from its preparation.

In another embodiment, a composition is provided consisting essentially of the crystalline form T1F-1/2 of Compound (I). The composition of this embodiment may comprise at least 90 weight percent of the crystalline form T1F-1/2 of Compound (I), based on the weight of Compound (I) in the composition. The remaining material comprises other form (s) of the compound and/or reaction impurities and/or processing impurities arising from its preparation.

The presence of reaction impurities and/or processing impurities may be determined by analytical techniques known in the art, such as, for example, chromatography, nuclear magnetic resonance spectroscopy, mass spectrometry, or infrared spectroscopy.

General Preparation of Crystalline Materials:

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture, High throughput crystallization techniques may be employed to prepare crystalline forms including polymorphs. Crystals of drugs, including polymorphs, methods of preparation, and characterization of drug crystals are discussed in *Solid-State Chemistry of Drugs*, S. R. Byrn, R. R. Pfeiffer, and J. G. Stowell, 2$^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369-377. In general, seeds of small size are needed to control effectively the growth of crystals in the batch. Seed of small size may be generated by sieving, milling, or micronizing of large crystals, or by microcrystallization of solutions. Care should be taken that milling or micronizing of crystals does not result in any change in crystallinity of the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, X-Ray powder diffraction, or the like, to assure formation of the preferred crystalline form of the product. The resulting crystalline form is typically produced in an amount of greater than about 70 weight percent isolated yield, preferably greater than 90 weight percent isolated yield, based on the weight of the compound originally employed in the crystallization procedure. The product may be co-milled or passed through a mesh screen to delump the product, if necessary.

Crystalline forms may be prepared directly from the reaction medium of the final process for preparing Compound (I). This may be achieved, for example, by employing in the final process step a solvent or a mixture of solvents from which Compound (I) may be crystallized. Alternatively, crystalline forms may be obtained by distillation or solvent addition techniques. Suitable solvents for this purpose include, for example, the aforementioned non-polar solvents and polar solvents, including protic polar solvents such as alcohols, and aprotic polar solvents such as ketones.

The presence of more than one polymorph in a sample may be determined by techniques such as powder X-Ray diffraction (PXRD) or solid state nuclear magnetic resonance spectroscopy (SSNMR), For example, the presence of extra peaks in an experimentally measured PXRD pattern when compared with a simulated PXRD pattern may indicate more than one polymorph in the sample. The simulated PXRD may be calculated from single crystal X-Ray data. see Smith, D. K., "*A FORTRAN Program for Calculating X-Ray Powder Diffraction Patterns*," Lawrence Radiation Laboratory, Livermore, Calif., UCRL-7196 (April 1963).

Characterization:

Form H-1 and Form T1F-1/2 of Compound (I) can be characterized using various techniques, the operation of which are well known to those of ordinary skill in the art. Examples of characterization methods include, but are not limited to, single crystal X-Ray diffraction, powder X-Ray diffraction (PXRD), simulated powder X-Ray patterns (Yin, S.; Scaringe, R. P.; DiMarco, J.; Galella, M. and Gougoutas, J. Z., *American Pharmaceutical Review*, 2003, 6, 2, 80), differential scanning calorimetry (DSC), solid-state $^{13}$C NMR (Earl, W. L. and Van der Hart, D. L., *J. Magn. Reson.*, 1982, 48, 35-54), Raman spectroscopy, infrared spectroscopy, moisture sorption isotherms, thermal gravimetric analysis (TGA), and hot stage techniques.

The H-1 form may be characterized and distinguished using single crystal X-Ray diffraction, which is based on unit cell measurements of a single crystal of Form H-1. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder X-Ray diffraction analysis in which the diffraction profile is compared to a simulated profile representing pure powder material, both run at the same analytical temperature, and measurements for the subject form characterized as a series of 2θ values.

One of ordinary skill in the art will appreciate that an X-Ray diffraction pattern may be obtained with a measurement of error that is dependent upon the measurement conditions employed. In particular, it is generally known that intensities in an X-Ray diffraction pattern may fluctuate depending upon measurement conditions employed. It should be further understood that relative intensities may also vary depending upon experimental conditions, and, accordingly, the exact order of intensity should not be taken into account. Additionally, a measurement error of diffraction angle for a conventional X-Ray diffraction pattern is typically about 5 percent or less, and such degree of measurement error should be taken into account as pertaining to the aforementioned diffraction angles. Consequently, it is to be understood that the crystal forms of the present disclosure are not limited to the crystal forms that provide X-Ray diffraction patterns completely identical to the X-Ray diffraction patterns depicted in the accompanying Figures disclosed herein. Any crystal form that provides an X-Ray diffraction pattern, DSC thermogram, or SSNMR spectrum substantially identical to those disclosed in the accompanying Figures falls within the scope of the present disclosure. The ability to ascertain substantial identities of X-Ray diffraction patters is within the purview of one of ordinary skill in the art.

Utility:

The H-1 and T1F-1/2 forms of Compound (I), alone or in combination with each other and/or other compounds, can be used to treat HCV infection.

The present disclosure also provides compositions comprising a therapeutically effective amount of Form H-1 and/or Form T1F-1/2 of Compound (I) and at least one pharmaceutically acceptable carrier.

The active ingredient, i.e., Form H-1 and/or Form T1F-1/2 of Compound (I), in such compositions typically comprises from 0.1 weight percent to 99.9 percent by weight of the composition, and often comprises from about 5 to 95 weight percent. In some cases, the pH of the formulation may be adjusted with pharmaceutically acceptable modifiers (such as calcium carbonate and magnesium oxide) to enhance the stability of the formulated compound or its delivery form. Formulations of the polymorph of the present disclosure may also contain additives for enhancement of absorption and bioavailability.

The pharmaceutical compositions of this disclosure may be administered orally, parenterally or via an implanted reservoir. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents and suspending agents. The details concerning the preparation of such compounds are known to those skilled in the art.

When orally administered, the pharmaceutical compositions of this disclosure may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, can also be added. For oral administration in a capsule form, useful carriers/diluents include lactose, high and low molecular weight polyethylene glycol, and dried corn starch. When aqueous suspensions are administered orally, the active ingredient is combined with emulsifying and suspending agents. If desired, certain sweetening and/or flavoring and/or coloring agents may be added.

Other suitable carriers for the above noted compositions can be found in standard pharmaceutical texts, e.g. in "Remington's Pharmaceutical Sciences", 19th ed., Mack Publishing Company, Easton, Pa., 1995. Further details concerning the design and preparation of suitable delivery forms of the pharmaceutical compositions of the disclosure are known to those skilled in the art.

Dosage levels of between about 0.05 and about 100 milligram per kilogram ("mg/kg") body weight per day, more specifically between about 0.1 and about 50 mg/kg body weight per day of the compounds of the disclosure are typical in a monotherapy for the prevention and/or treatment of HCV mediated disease. Typically, the pharmaceutical compositions of this disclosure will be administered from about 1 to about 3 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, gender, diet, time of administration, the duration of treatment, rate of excretion, drug combination, the severity and course of the infection, the patient's disposition to the infection and the judgment of the treating physician. In one embodiment, unit dosage formulations are those containing a daily dose or sub-dose, as herein above recited, or an appropriate fraction thereof, of an active ingredient. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of the polymorph of the disclosure and one or more additional therapeutic or prophylactic agents, both the compound and the additional agent are usually present at dosage levels of between about 10 and 100 percent, and more preferably between about 10 and 80 percent of the dosage normally administered in a monotherapy regimen. Administration of the one or more additional agents may occur prior to, after, or simultaneously with the polymorph of the present disclosure.

When the polymorph is formulated together with a pharmaceutically acceptable carrier, the resulting composition may be administered in vivo to mammals, such as man, to inhibit NS3/4A or to treat or prevent HCV virus infection. Such treatment may also be achieved using the polymorph of this disclosure in combination with agents which include, but are not limited to: Immunomodulatory agents, such as interferons; other antiviral agents such as ribavirin, amantadine; other inhibitors of NS3/4A; inhibitors of other targets in the HCV life cycle such as helicase, polymerase, metalloprotease, or internal ribosome entry site; or combinations thereof. The additional agents may be combined with the polymorph of this disclosure to create a single dosage form. Alternatively these additional agents may be separately administered to a mammal as part of a multiple dosage form.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |

TABLE 1-continued

| Brand Name | Physiological Class | Type of Inhibitor or Target | Source Company |
|---|---|---|---|
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |

TABLE 1-continued

| Brand Name | Physiological Class | Type of Inhibitor or Target | Source Company |
|---|---|---|---|
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |

TABLE 1-continued

| Brand Name | Physiological Class | Type of Inhibitor or Target | Source Company |
|---|---|---|---|
| GL-59728 | Antiviral | NS5B Replicase Inhibitor | Genelabs |
| ANA-971 | Antiviral | TLR-7 agonist | Anadys |
| TMC-465350 | Antiviral | serine protease inhibitor | Medivir/ Tibotec |

Another aspect of this disclosure provides methods of inhibiting HCV NS3 activity in patients by administering the polymorph of the present disclosure.

In one embodiment, these methods are useful in decreasing HCV NS3 activity in the patient. If the pharmaceutical composition comprises only the polymorph of this disclosure as the active component, such methods may additionally comprise the step of administering to said patient an agent selected from an immunomodulatory agent, an antiviral agent, an HCV NS3 inhibitor, or an inhibitor of other targets in the HCV life cycle such as, for example, helicase, polymerase, protease, or metalloprotease. Such additional agent may be administered to the patient prior to, concurrently with, or following the administration of the compounds of this disclosure.

In another embodiment, these methods are useful for inhibiting viral replication in a patient. Such methods can be useful in treating or preventing HCV disease.

The polymorphs of the disclosure may also be used as a laboratory reagent. The polymorphs may be instrumental in providing research tools for designing of viral replication assays, validation of animal assay systems and structural biology studies to further enhance knowledge of the HCV disease mechanisms.

The polymorphs of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

The following non-limiting examples are illustrative of the disclosure.

EXAMPLES

Example 1

Preparation of Form H-1/T1F-1/2

Amorphous N-(tert-butoxycarbonyl)-3-methyl-L-valyl-(4R)-4-((7-chloro-4-methoxy-1-isoquinolinyl)oxy)-N-((R, 2S)-1-((cyclopropylsulfonyl)carbamoyl)-2-vinylcyclopropyl)-L-prolinamide prepared according to the procedure described in U.S. Pat. No. 6,995,174) is stirred or sonicated in ethanol at room temperature with a concentration of 8-10 ml solvent/g compound. The solid first dissolves instantly in the solution and then forms a slurry within several minutes of agitation. The crystal form obtained from the slurry is a solvate (Form E2-2). The slurry is isolated and dried at 50° C. under vacuum, resulting in the formation of T1F-1/2. The T1F-1/2 form can transform to H-1, resulting in either a mixture of both forms or conversion to Form H-1, depending on the ambient humidity and temperature conditions.

Crystalline N-(tert-butoxycarbonyl)-3-methyl-L-valyl-(4R)-4-((7-chloro-4-methoxy-1-isoquinolinyl)oxy)-N-((1R, 2S)-1-((cyclopropylsulfonyl)carbamoyl)-2-vinylcyclopropyl)-L-prolinamide is dissolved in ethanol at 50° C. with a concentration of 10-12 ml solvent/g compound. (Heptane can be added to the solution at 50° C. at this stage.) The agitated batch is gradually cooled down to 20° C. and aged to develop crystallization. Seeding is optional; it is seeded between 45° C. and 20° C. to form slurry. The crystal form obtained from the slurry is a solvate. The slurry is then filtered and the solid obtained is dried at 50° C. under vacuum, resulting in the formation of T1F-1/2. The T1F-1/2 form can transform to H-1, resulting in either a mixture of both forms or conversion to Form H-1, depending on the ambient humidity and temperature conditions.

Solid-state Transformation Via Gas-solid Hydration

The hydrate H-1 can be prepared by converting the free acid T1F-112 via hydration with humid air or nitrogen under controlled conditions. The T1F-1/2 form in contact with a humidified air or nitrogen flow transforms into the hydrate over a period of time (flow rate 300-1000 ml/min, RH>90%, within 24 hrs at room temp). It is also observed that by drying the E2-2 wet cake isolated from crystallization under flowing air or nitrogen at ambient conditions (RH 40-80%, room temp) will eventually convert the solvate to the hydrate.

Slurry Conversion of Hydrate in Crystallization

Crystallization was prepared in varying compositions of EtOH and water to examine the crystal form(s) obtained and evaluated the feasibility for achieving hydrate directly in the slurry. A high water activity is needed to form hydrate in the slurry conversion: E2-2 wet cake reslurried in water over a period of time at 20-50° C. converts to the hydrate with residual E2-2 present in the slurry. This procedure may also apply to other alcohol solvates (e.g., M-1, methanolate) in transforming into the hydrate in a water containing slurry.

Example 2

Alternative Preparation of Form H-1 and/or T1F-1/2

Amorphous N-(tert-butoxycarbonyl)-3-methyl-L-valyl-(4R)-4-((7-chloro-4-methoxy-1-isoquinolinyl)oxy)-N-((1R, 2S)-1-((cyclopropylsulfonyl)carbamoyl)-2-vinylcyclopropyl)-L-prolinamide (prepared according to the procedure described in U.S. Pat. No. 6,995,174) is stirred or sonicated in isopropyl alcohol at room temperature with a concentration of 5-14 ml solvent/g compound. The solid first dissolves with or without agitation in the solution and then forms a slurry within several minutes. The crystal form obtained from the slurry is a solvate. The slurry is isolated and dried at 50° C. under vacuum, resulting in the formation of T1F-1/2. The T1F-1/2 form can transform to H-1, subject to the ambient humidity and temperature conditions. The T1F-1/2 form can transform to H-1, resulting in either a mixture of both forms or conversion to Form H-1, depending on the ambient humidity and temperature conditions.

Crystalline N-(tert-butoxycarbonyl)-31-methyl-L-valyl-(4R)-4-((7-chloro-4-methoxy-1-isoquinolinyl)oxy)-N-((1R, 2S)-1-((cyclopropylsulfonyl)carbamoyl)-2-vinylcyclopropyl)-L-prolinamide is dissolved in isopropyl alcohol at 50-60° C. with a concentration of 15-17 ml solvent/g compound. (Water can be added to the solution at 60° C. at this stage). Seeding is optional. The agitated batch is gradually cooled down to 20° C. and aged to develop crystallization. The crystal form obtained from the slurry is a solvate. The slurry is then filtered and the solid obtained is dried at 50° C. under vacuum, resulting in the formation of T1F-1/2. The T1F-1/2 form can transform to H-1, subject to the ambient humidity and temperature conditions. The T1F-1/2 form can transform to H-1, resulting in either a mixture of both forms or conversion to Form H-1, depending on the ambient humidity and temperature conditions.

Example 3

Alternative Preparation of Form H-1

Crystals of H-1 were also prepared as follows: The compound (amorphous or crystalline) was dissolved in methanol. Water was added as an anti-solvent. Prism or plate-shaped crystals were obtained which were a 1:1 methanol solvate. These crystals were left under ambient conditions and converted to Form H-1 via slow solvent exchange between methanol in the crystals and moisture in the air.

Example 4

Alternative Preparation of Form T1F-1/2

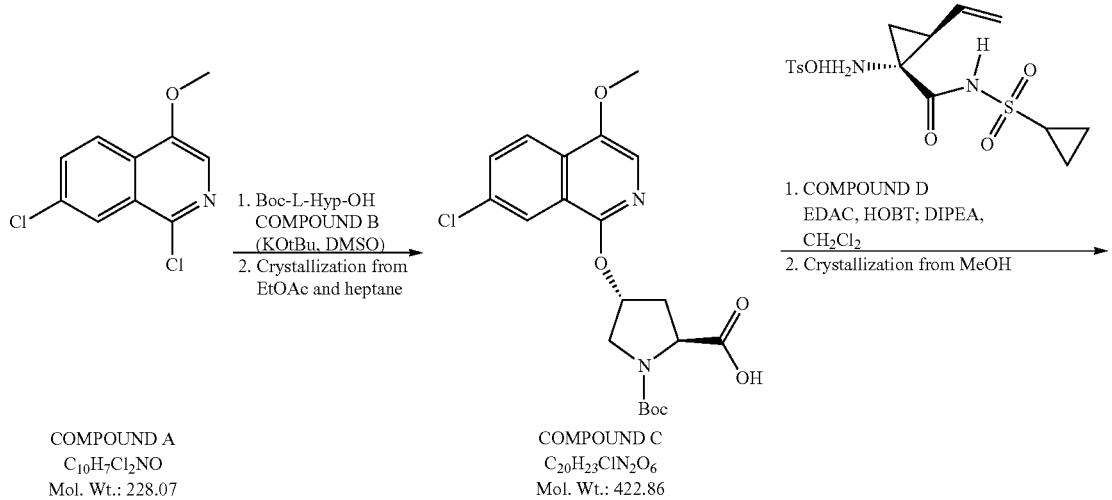

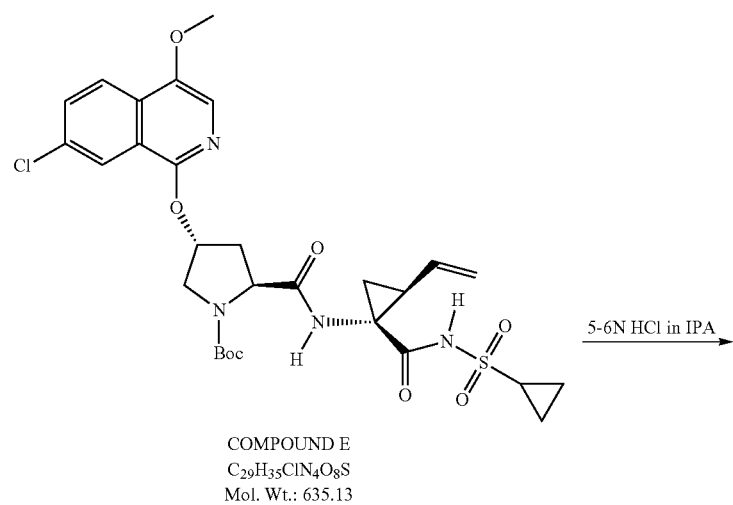

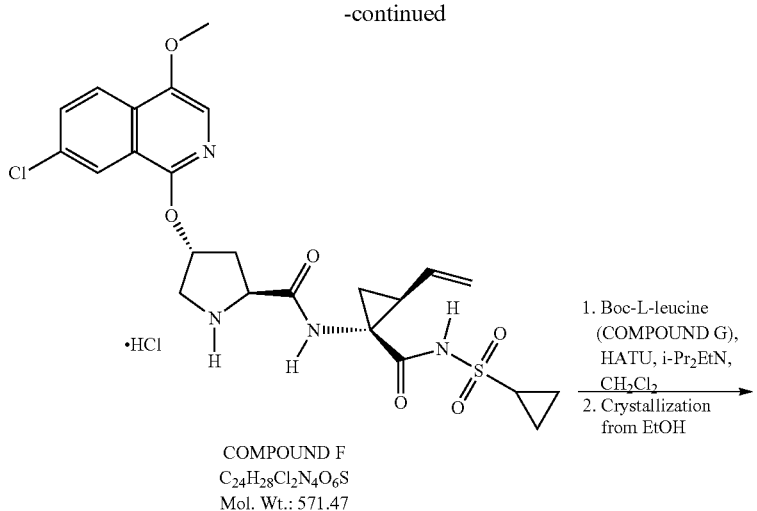

COMPOUND F
C₂₄H₂₈Cl₂N₄O₆S
Mol. Wt.: 571.47

1. Boc-L-leucine (COMPOUND G), HATU, i-Pr₂EtN, CH₂Cl₂
2. Crystallization from EtOH

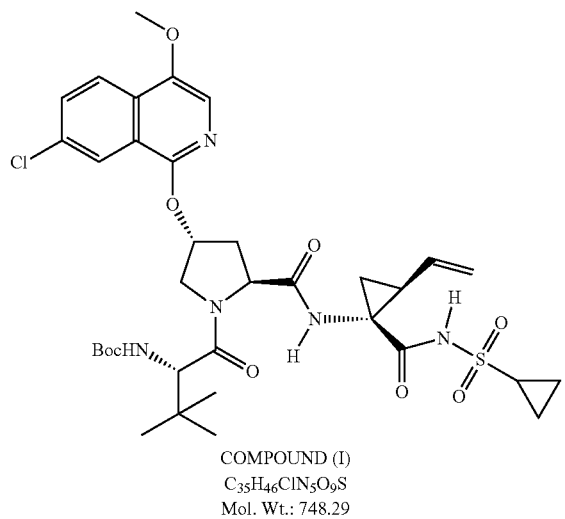

COMPOUND (I)
C₃₅H₄₆ClN₅O₉S
Mol. Wt.: 748.29

Preparation of Compound C

DMSO (264 ml) was added to a mixture of Compound A (6 g, 26.31 mmol, 1.0 eq, 96.5% potency), Compound B (6.696 g, 28.96 mmol, 1.1 eq) and KOtBu (8.856 g, 78.92 mmol, 3 eq) under nitrogen and stirred at 36° C. for 1 h. After cooling the dark solution to 16° C., it was treated with water (66 ml) and EtOAc (132 ml). The resulting biphasic mixture was acidified to pH 4.82 with 1N HCl (54 ml) at 11.2-14.6° C. The phases were separated. The aqueous phase was extracted once with EtOAc (132 ml). The organic phases were combined and washed with 25% brine (2×132 ml). Rich organic phase (228 ml) was distilled at 30-40° C./50 mbar to 37.2 ml. A fresh EtOAc (37.2 ml) was added and distilled out to 37.2 ml at 30-35° C./50 nm bar. After heating the final EtOAc solution (37.2 ml) to 50° C., heptane ((37.2 ml) was added at 46-51° C. and cooled to 22.5° C. over 2 h. It was seeded with 49 mg of Compound C and held at 23° C. for 15 min to develop a thin slurry. It was cooled to 0.5° C. in 30 min and kept at 0.2-0.5° C. for 3 h. After the filtration, the cake was washed with heptane (16.7 ml) and dried at 47° C./80 mm/15.5 h to give Compound C as beige colored solids (6.3717 g, 58.9% corrected yield, 99.2% potency, 97.4 AP).

Preparation of Compound E

DIPEA (2.15 ml, 12.3 mmol, 1.3 eq followed by EDAC (2 g, 10.4 mmol, 1.1 eq) were added to a mixture of Compound C (4 g, 9.46 mmol, 97.4% potency, 98.5 AP), Compound D (4.568 g, 11.35 mmol, 1.20 eq), HOBT-H2O (0.86 g, 4.18 mmol, 0.44 eq) in CH₂Cl₂ (40 ml) at 23-25° C. under nitrogen. The reaction was complete after 3 h at 23-25° C. It was then washed with 1N HCl (12 ml), water (12 ml) and 25% brine (12 ml). MeOH (80 ml) was added to the rich organic solution at 25° C., which was distilled at atmospheric pressure to ~60 ml to initiate the crystallization of the product. The crystal slurry was then cooled from 64° C. to 60° C. in 5 min and stirred at 60° C. for 1 h. It was further cooled to 24° C. over 1.5 h and held at 24° C. for 2 h. After the filtration, the cake was washed with MeOH (12 ml) and dried at 51° C./20-40 nm i/18 h to give Compound E (5.33 g, 89% yield, 97.7% potency, 99.1 AP).

Preparation of Compound F 5-6N HCl in IPA (10.08 ml, 50.5 mmol, Normality: 5N) was added in four portions in 1 h to a solution of Compound E (8 g, 12.6 mmol, 97.7% potency, 99.1 AP) in IPA (120 ml) at 75° C. After stirring for 1 h at 75° C., the resulting slurry was cooled to 21° C. in 2 h and stirred at 21° C. for 2 h. It was filtered and the cake was washed with IPA (2×24 ml). The wet cake was dried at 45° C./House vacuum/16 h to give Compound F as an off-white solid (6.03 g, 84.5% yield, 98.5% potency, 100 AP).

Preparation of Compound (I)

DIPEA (9.824 ml) followed by HATU (7.99 g) were added to a stirred mixture of Compound F (10 g, 99.2% potency, 99.6 AP) and Compound G (4.41 g) in $CH_2Cl_2$ (100 ml) at 2.7-5° C. under nitrogen. The resulting light brown solution was stirred at 0.2-3° C. for 1.5 h, at 3-20° C. in 0.5 h and at 20-23° C. for 15.5 h for a reaction completion. It was quenched with 2N HCl (50 ml) at 23° C. and stirred for 20 min at 23-24° C. The biphasic mixture was polish filtered through diatomaceous earth (Celite®) (10 g) to remove insoluble solids of HOAT and HATU. The filter cake was washed with 20 ml of $CH_2Cl_2$. After separating the organic phase from the filtrates, it was washed with 2N HCl (5×50 ml) and water (2×50 ml). The organic phase (115 ml) was concentrated to ~50 ml, which was diluted with absolute EtOH (200 proof, 100 ml) and concentrated again to ~50 ml. Absolute EtOH (50 ml) was added to bring the final volume to 100 ml. It was then warmed to 50° C. to form a clear solution and held at 50° C. for 35 min. The ethanolic solution was cooled from 50 to 23° C. over 15 min to form the crystal slurry. The slurry was stirred at 23 CC for 18 h, cooled to 0.3° C. over 30 min and kept at 0.2-0.3° C. for 2 h. After the filtration, the cake was washed with cold EtOH (2.7° C., 2×6 ml) and dried at 53° C./72 mm/67 h to give Compound (I) in Form T1F-1/2 as an off white solid (10.49 g, 80.7% yield, 99.6 AP).

Forms H-1 and T1F-1/2 were analyzed using one or more of the testing methods described below.

1 Single Crystal X-Ray Measurements

A Nonius Kappa CCD diffractometer equipped with graphite-monochromated Mo Kα radiation (λ=0.7107 Å) was used to collect diffraction data at room temperature. A full data set was collected using the ω scan mode over the 2θ range and processed using the routine associated with the diffractometer system (Kappa CCD Software, Nonius BV, Delft, The Netherlands, 1999). The final unit cell parameters were determined using the entire data set. All structures were solved by direct methods and refined by the full-matrix least-squares techniques, using the SHELXTL software package (Sheldrick, GM. 1997, SHELTL. Structure Determination Programs. ersion 5.10, Bruker AXS, Madison, Wis., USA). The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$, where w is an appropriate weighting function based on errors in the observed intensities. Difference Fourier maps were examined at all stages of refinement. All non-hydrogen atoms were refined with anisotropic thermal displacement parameters. The hydrogen atoms associated with hydrogen bonding were located in the final difference Fourier maps while the positions of the other hydrogen atoms were calculated from an idealized geometry with standard bond lengths and angles. They were assigned isotropic temperature factors and included in structure factor calculations with fixed parameters.

The crystal data of the H-1 form is shown in Table 2. The fractional atomic coordinates are listed in Table 3. It should be understood by one of ordinary skill in the art that slight variations in the coordinates are possible and are considered to be within the scope the present disclosure.

TABLE 2

Crystal Data of Form H-1

| Temperature | room temperature |
|---|---|
| Wavelength | 0.7107 Å |
| Crystal system, space group | Orthorhombic |
| Unit cell dimensions | a = 10.0802(1) Å alpha = 90.00° |
| | b = 16.6055(2) Å beta = 90.00° |
| | c = 24.9294(3) Å gamma = 90.00° |
| Volume | 4172.85(8) Å³ |
| Z, Calculated density | 4, 1.220 Mg/m³ |

TABLE 3

Atomic coordinates

| Atom | X | Y | Z |
|---|---|---|---|
| S(1) | 4633(2) | 1649(1) | 6093(1) |
| N(1) | 4351(5) | 2223(2) | 5569(2) |
| N(2) | 3770(4) | 3280(2) | 4728(1) |
| N(3) | 3590(4) | 4937(2) | 5607(2) |
| N(4) | 2677(6) | 4277(4) | 6916(2) |
| O(1) | 3677(8) | 1898(3) | 6465(2) |
| O(2) | 5997(7) | 1682(4) | 6230(3) |
| O(3) | 5891(4) | 1613(2) | 5053(2) |
| O(4) | 5570(3) | 3910(2) | 5093(2) |
| O(5) | 3215(3) | 3701(2) | 5941(1) |
| O(6) | 1838(7) | 5342(6) | 7297(3) |
| O(7) | 965(8) | 4111(6) | 7476(3) |
| O(8) | 2101(3) | 6221(2) | 4962(2) |
| C(1) | 2870(11) | 464(5) | 5759(4) |
| C(2) | 4303(8) | 668(3) | 5873(3) |
| C(3) | 3535(11) | 137(4) | 6251(3) |
| C(4) | 5005(5) | 2093(3) | 5089(2) |
| C(5) | 4463(4) | 2547(3) | 4620(2) |
| C(6) | 5213(6) | 2451(3) | 4100(2) |
| C(7) | 3892(6) | 2041(3) | 4159(2) |
| C(8) | 3733(7) | 1146(4) | 4208(2) |
| C(9) | 4597(9) | 621(4) | 4048(5) |
| C(10) | 4385(4) | 3907(2) | 4968(2) |
| C(11) | 3500(4) | 4639(2) | 5061(2) |
| C(12) | 3970(6) | 5355(3) | 4730(2) |
| C(13) | 3495(5) | 6077(3) | 5045(2) |
| C(14) | 3637(6) | 5819(3) | 5640(2) |
| C(15) | 3451(5) | 4424(3) | 6021(2) |
| C(16) | 3606(6) | 4702(3) | 6603(2) |
| C(17) | 5104(7) | 4618(4) | 6797(3) |
| C(18) | 5991(7) | 5136(5) | 6512(3) |
| C(19) | 5075(13 | 4835(6) | 7407(3) |
| C(20) | 5573(8) | 3749(5) | 6748(4) |
| C(21) | 1764(11 | 4565(8) | 7247(3) |
| C(26) | 1723(7) | 6568(3) | 4504(2) |
| N(5) | 2626(8) | 6756(3) | 4152(2) |
| C(27) | 2129(14) | 7105(5) | 3682(3) |
| C(28) | 820(19) | 7272(4) | 3590(3) |
| C(29) | −131(13) | 7075(3) | 3984(3) |
| C(30) | 304(8) | 6707(3) | 4469(3) |
| C(31) | −584(7) | 6494(3) | 4875(3) |
| C(32) | −1848(7) | 6620(4) | 4807(5) |
| C(33) | −2325(15) | 6965(6) | 4310(7) |
| C(34) | −1576(17) | 7197(5) | 3918(5) |
| Cl(1) | −2988(2) | 6335(2) | 5319(2) |
| C(4') | −530(14) | 5479(13) | 7544(9) |
| C(3') | 1250(30) | 6541(9) | 7751(10) |
| C(2') | 1088(19) | 5236(10) | 8267(5) |
| C(1') | 921(17) | 5659(9) | 7735(6) |
| O(28) | 253(10) | 7631(5) | 3159(3) |
| C(281 | 1165(18) | 7762(10) | 2753(6) |
| OW | 1760(70) | 6690(30) | 6150(30) |

2. Powder X-Ray Diffraction

X-Ray powder diffraction (PXRD) data were obtained using a Bruker C2 GADDS. The radiation was Cu Kα (40 KV, 50 mA). The sample-detector distance was 15 cm. Powder samples were placed in sealed glass capillaries of 1 mm or less in diameter; the capillary was rotated during data collection. Data were collected for 3≦2θ≦35° with a sample exposure time of at least 2000 seconds. The resulting two-dimensional diffraction arcs were integrated to create a traditional 1-dimensional PXRD pattern with a step size of 0.02 degrees 2θ in the range of 3 to 35 degrees 2θ.

Figure 2:
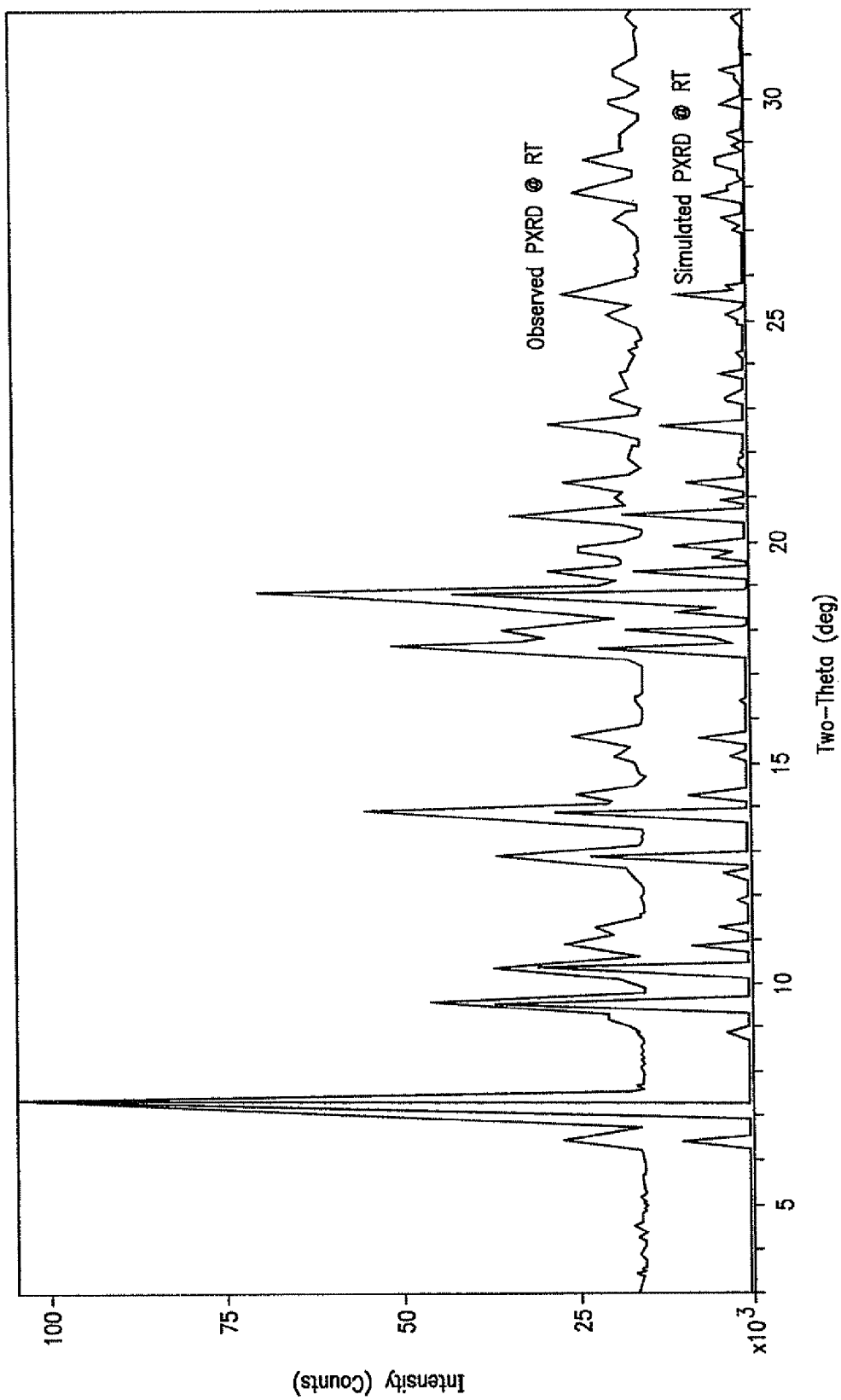
FIG. 2 illustrates experimental and simulated powdered X-Ray diffraction patterns (CuKα λ=1.54178 Å at T=room temperature) of the H-1 crystalline form of Compound (I).

The results of the PXRD pattern and a simulated pattern calculated from the single crystal data for Form H-1 are shown in FIG. 2.

Figure 3:
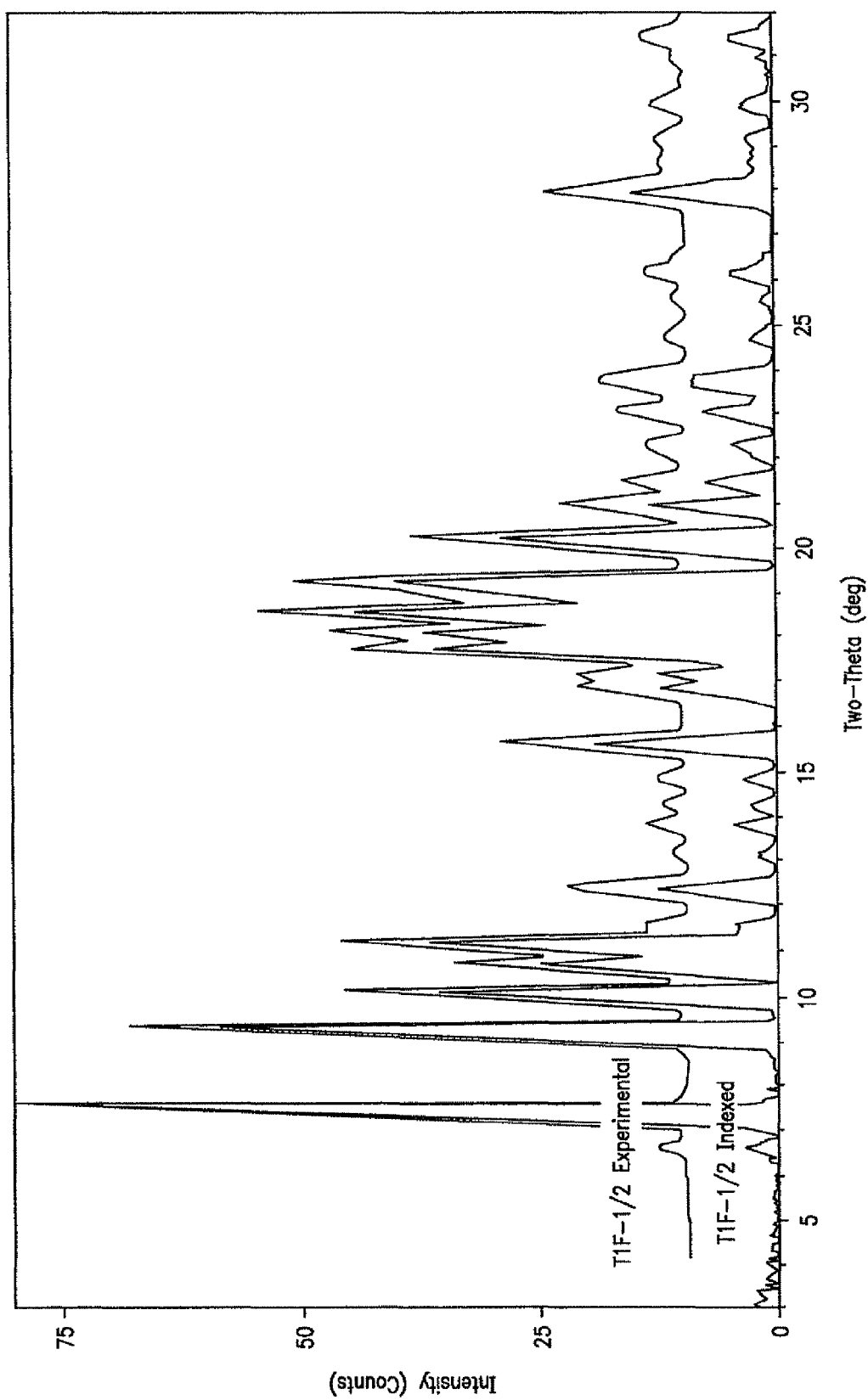
FIG. 3 illustrates experimental and indexed powdered X-Ray diffraction patterns (CuKα λ=1.54178 Å at T=room temperature) of the T1F-1/2 crystalline form of Compound (I).

The results of the PXRD pattern for Form T1F-1/2 is shown in FIG. 3.

Figure 4:
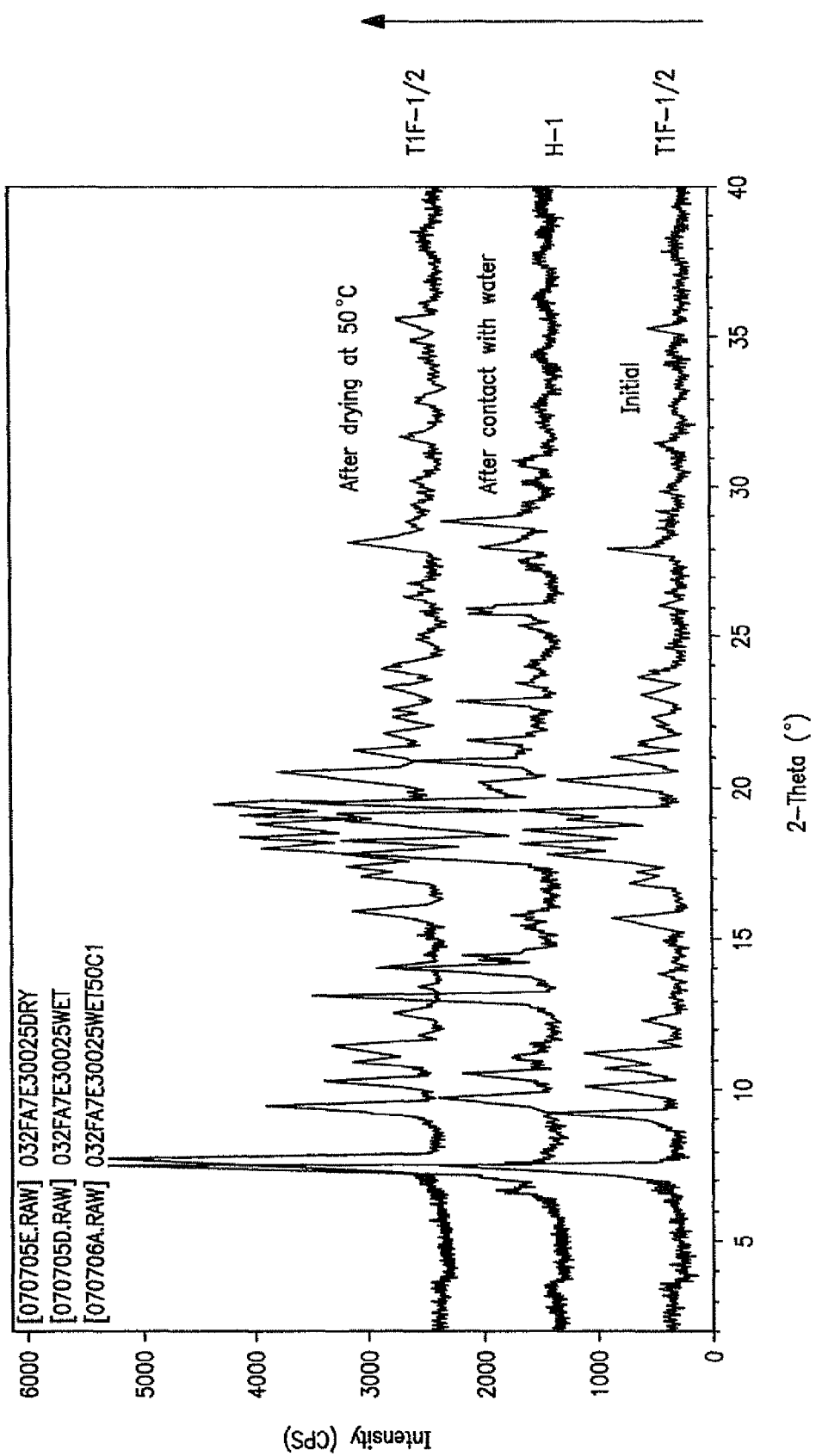
FIG. 4 illustrates the powdered X-Ray diffraction analysis of T1F-1/2 and H-1 form interconversion.

FIG. 4 shows the PXRD analysis of Form T1F-1/2 and Form H-1 interconversion.

Table 4 lists the characteristic PXRD peaks that describe Forms H-1 and T1F-1/2 of Compound (I).

TABLE 4

Characteristic diffraction peak positions (degrees 2θ ± 0.1) at room temperature, based on a high quality pattern collected with a diffractometer (cuKα) with a spinning capillary with 2θ calibrated with a NIST traceable standard.

| Form H-1 | Form T1F-1/2 |
|---|---|
| 6.3 | 7.3 |
| 7.1 | 9.1 |
| 9.4 | 10.0 |
| 10.3 | 10.6 |
| 12.7 | 11.1 |
| 13.8 | 12.3 |
| 17.5 | 15.6 |
| 18.7 | 20.1 |
| 20.6 | 20.9 |
| 22.5 | 27.8 |

3. Differential Scanning Calorimetry

Differential scanning calorimetry (DSC) experiments were performed in a TA Instruments™ model Q2000, Q1000 or 2920. The sample (about 2-6 mg) was weighed in an aluminum pan and recorded accurately to a hundredth of a milligram, and transferred to the DSC. The instrument was purged with nitrogen gas adt 50 mL/min. Data were collected between room temperature and 300° C. at 10° C./min heating rate. The plot was made with the endothermic peaks pointing down.

Figure 5:
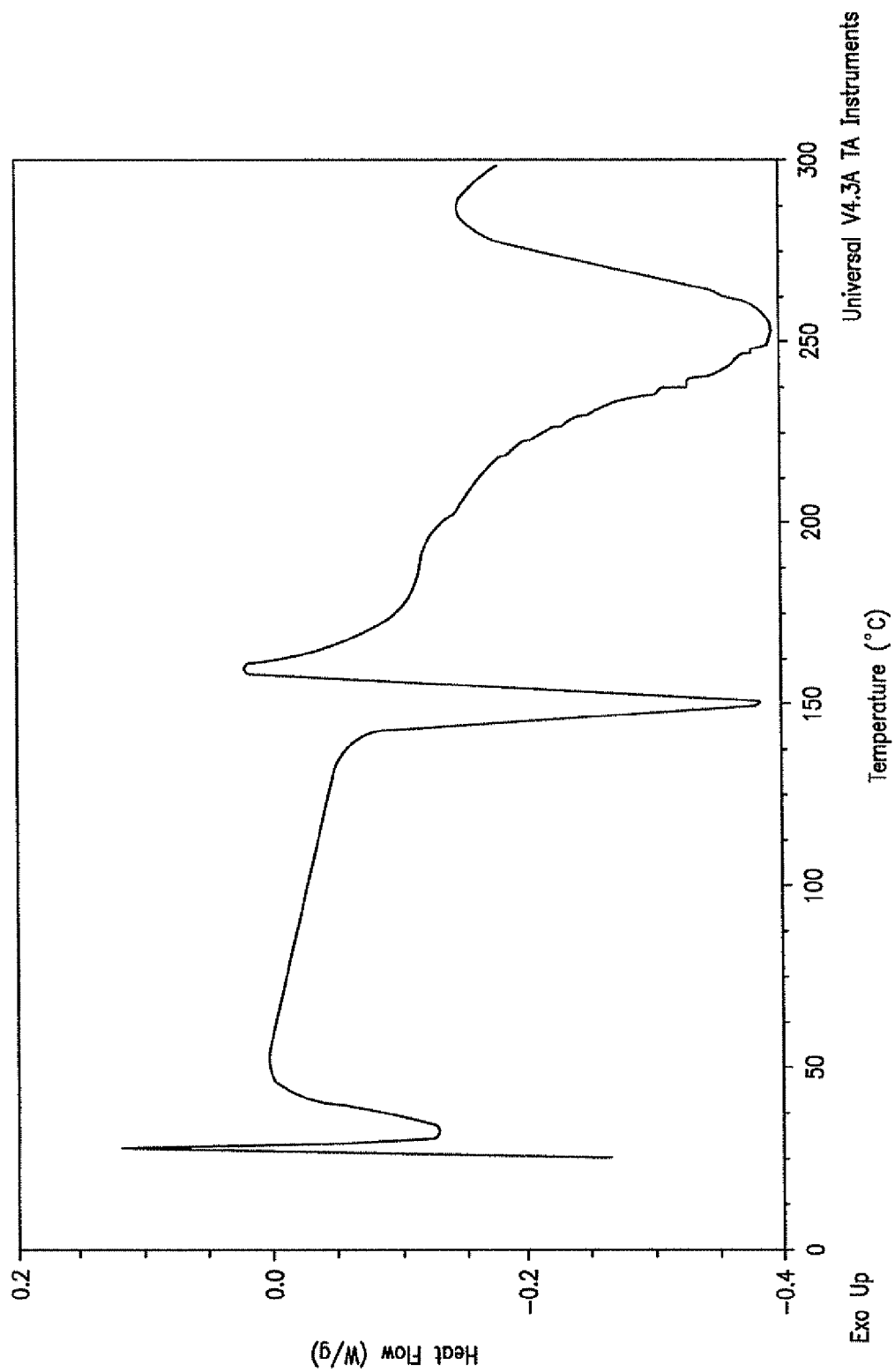
FIG. 5 illustrates the differential scanning calorimetry pattern of the H-1 crystalline form of Compound (I).
Figure 6:
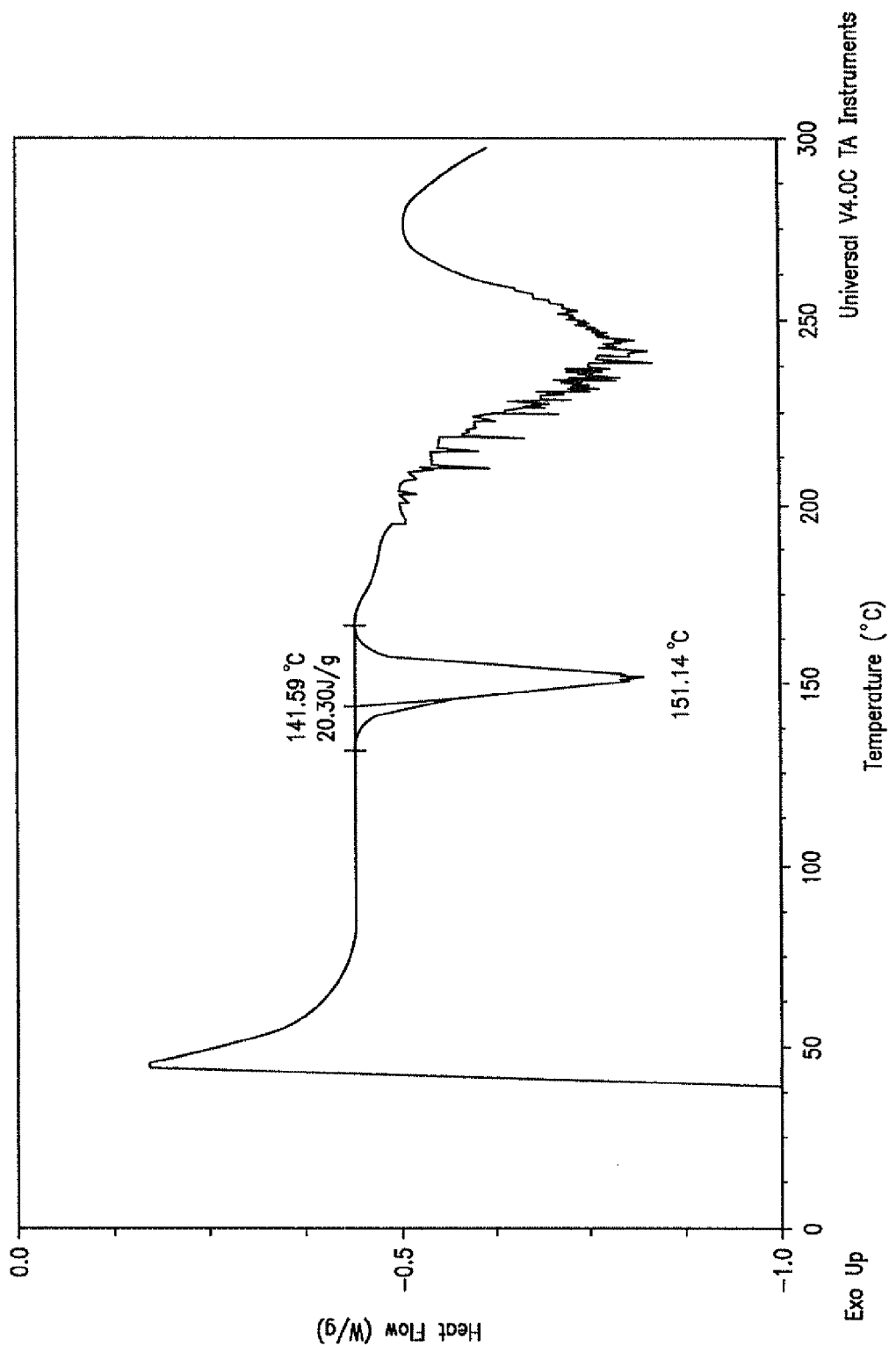
FIG. 6 illustrates the differential scanning calorimetry pattern of the T1F-1/2 crystalline form of Compound (I).

The DSC pattern of Form H-1 is shown in FIG. 5. The DSC pattern of Form T1F-1/2 is shown in FIG. 6.

4. Solid-State NMR (SSNMR)

All solid-state C-13 NMR measurements were made with a Bruker DSX-400, 400 MHz NMR spectromter. High resolution spectra were obtained using high-power proton decoupling and the TPPM pulse sequence and ramp amplitude cross-polarization (RAMP-CP) with magic-angle spinning (MAS) at approximately 12 kHz (A. E. Bennett et al. *J. Chem. Phys.* 1995, 103, 6951). (G. Metz, X. Wu, and S. O. Smith, *J. Magn. Reson. A.,* 1994, 100, 219-227). Approximately 70 mg of sample, packed into a canister-design zirconia rotor was used for each experiment. Chemical shifts (δ) were referenced to external adamantane with the high frequency resonance being set to 38.56 ppm (W. L. Earl and D. L. VanderHart, *J. Magn. Reson.,* 1982, 48, 35-54).

Figure 7:
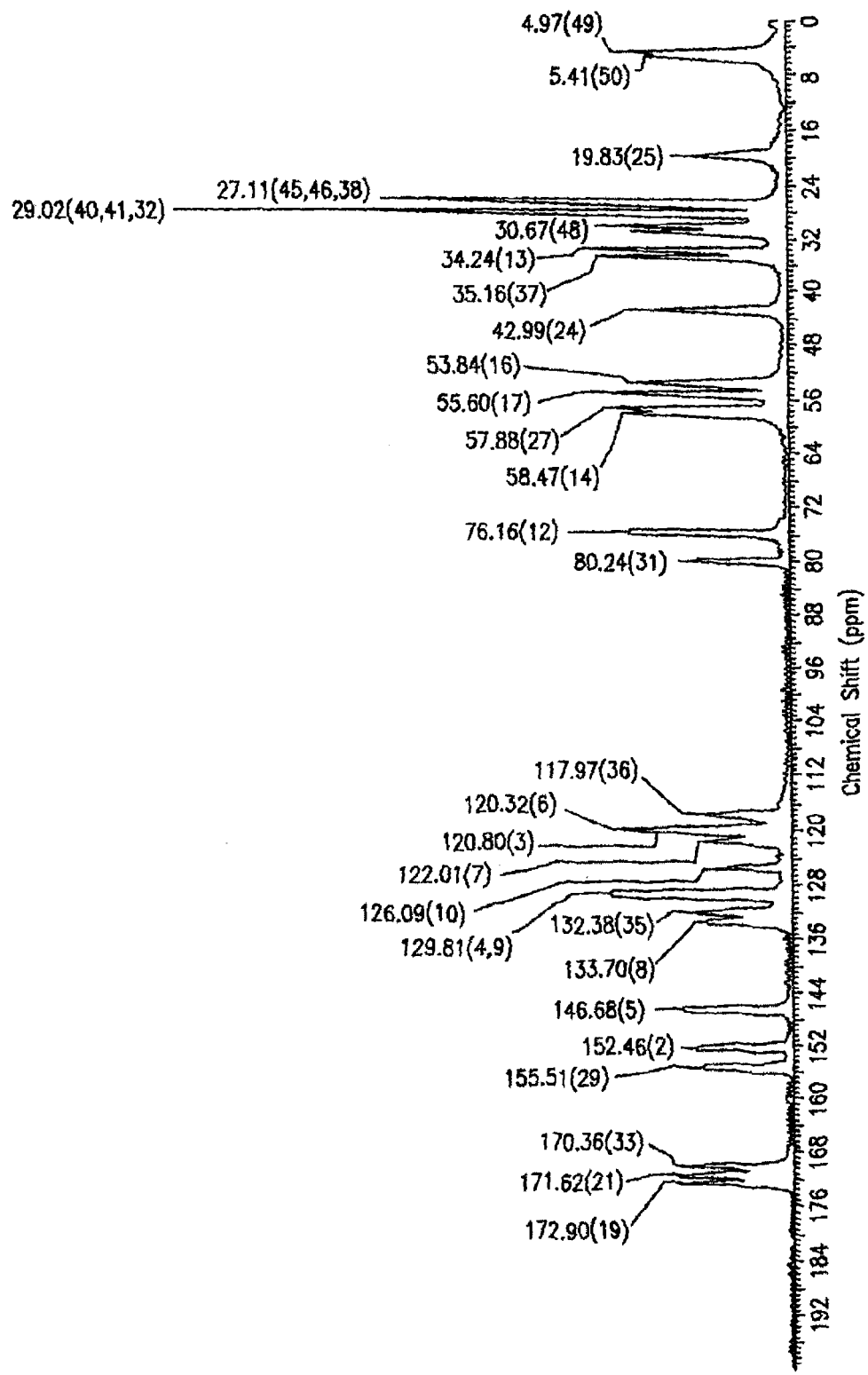
FIG. 7 illustrates the solid state NMR spectrum of the T1F-1/2 crystalline form of Compound (I).
Figure 8:
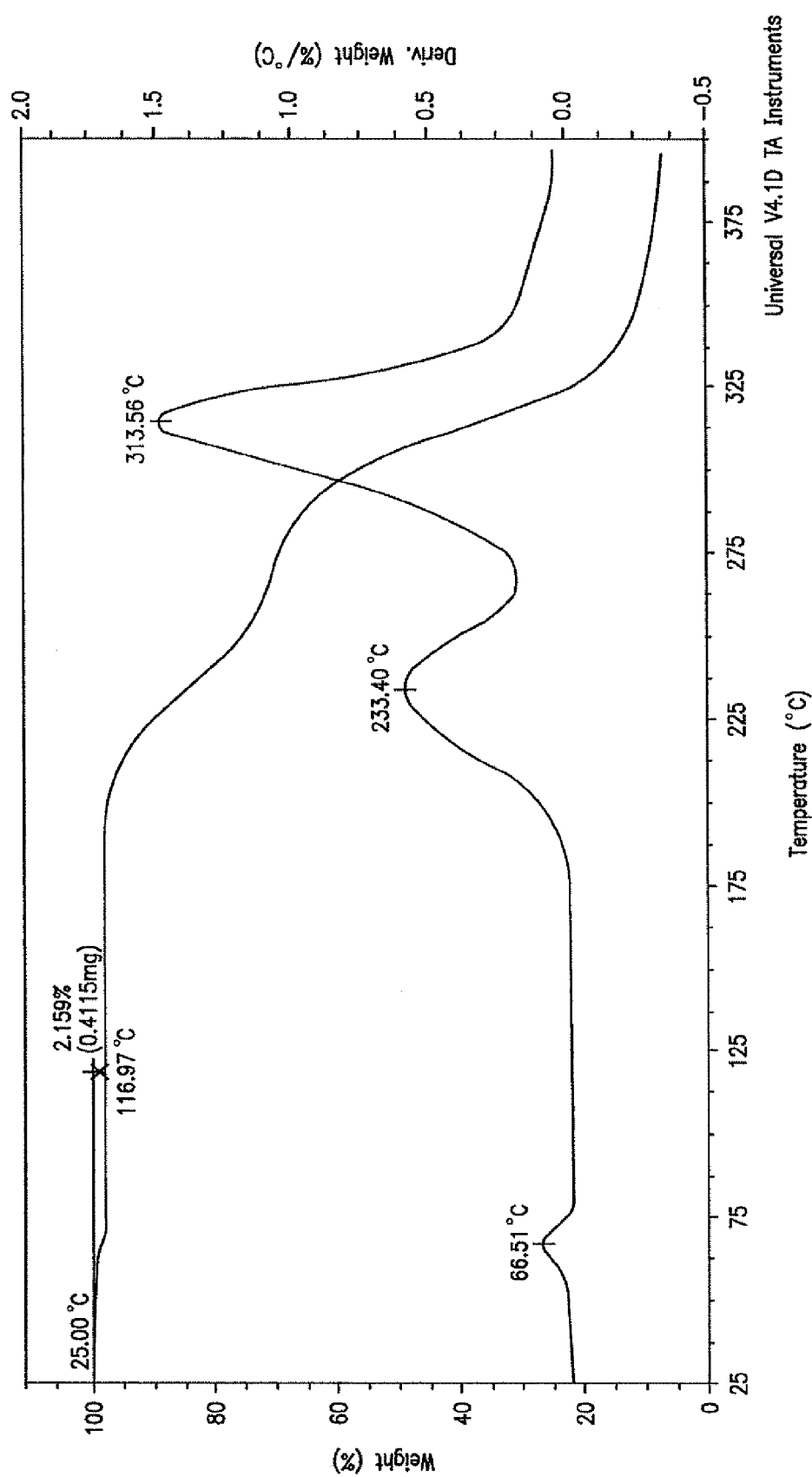
FIG. 8 illustrates the thermal gravimetricy analysis pattern of the H-1 crystalline form of Compound (I).

The SSNMR spectra for Form T1F-1/2 is shown in FIG. 7.

5. Thermal Gravimetric Analysis (TGA) (Open Pan)

Thermal gravimetric analysis (TGA) experiments were performed in a TA Instruments™ model Q500 or 2950, The sample (about 10-30 mg) was placed in a platinum pan previously tared. The weight of the sample was measured accurately and recorded to a thousand of a milligram by the instrument. The furnace was purged with nitrogen gas at 100 mL/min. Data were collected between room temperature and 300° C. at 10° C./min heating rate.

Figure 9:
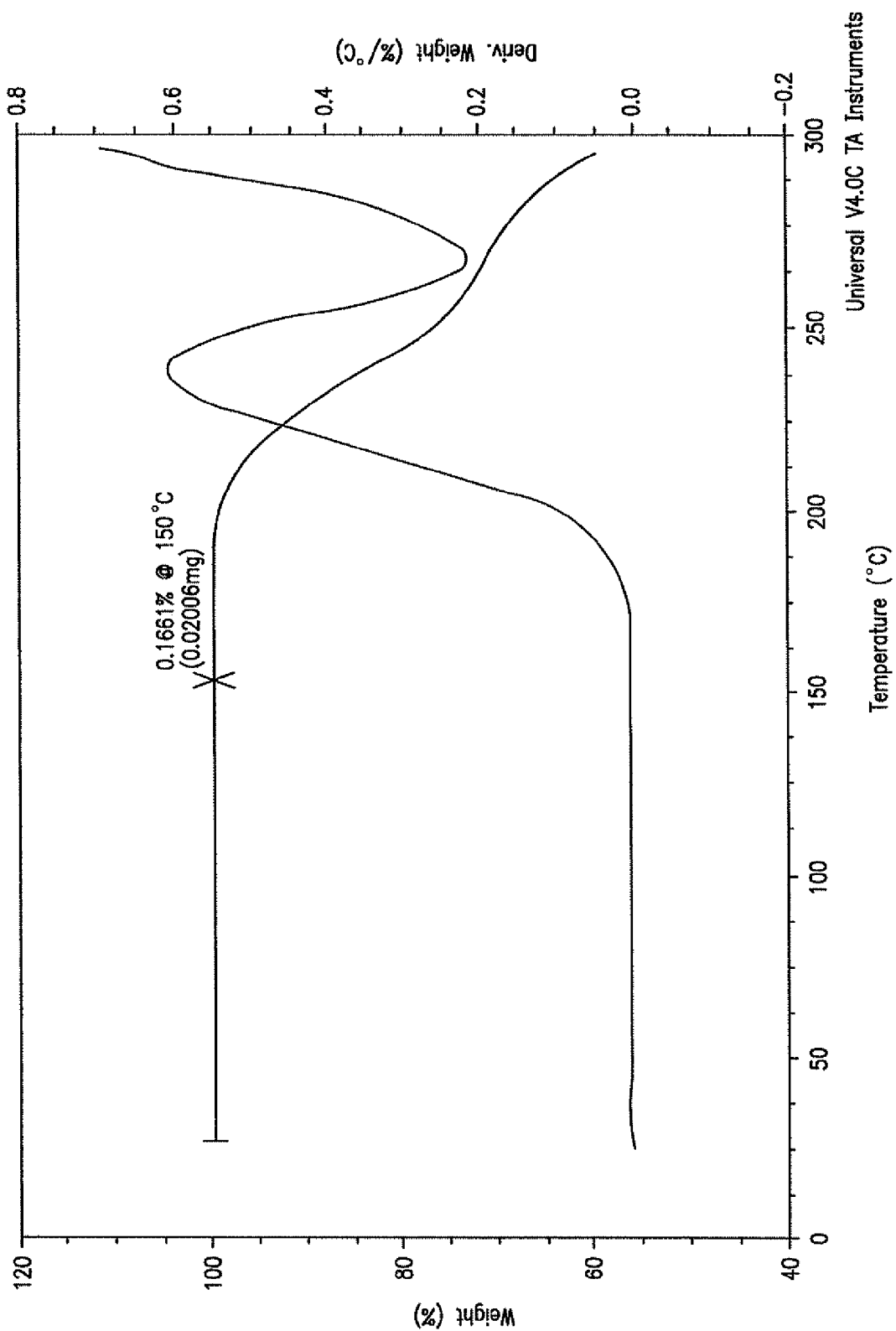
FIG. 9 illustrates the thermal gravimetricy analysis pattern of the T1F-1/2 crystalline form of Compound (I).

The TGA patterns of Form H-1 and Form T1F-1/2 are shown in FIG. 9 and FIG. 10, respectively.

What is claimed is:

1. Form H-1 of

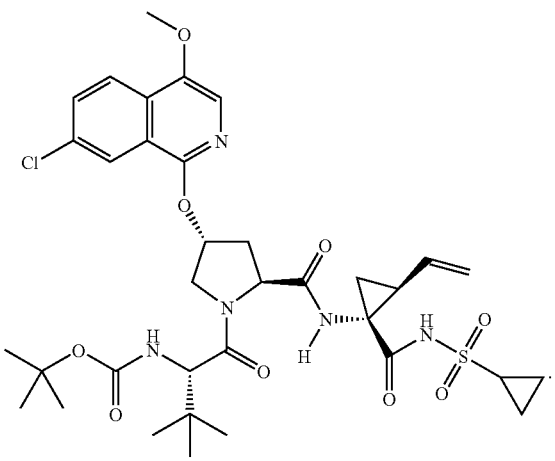

2. Form H-1 of

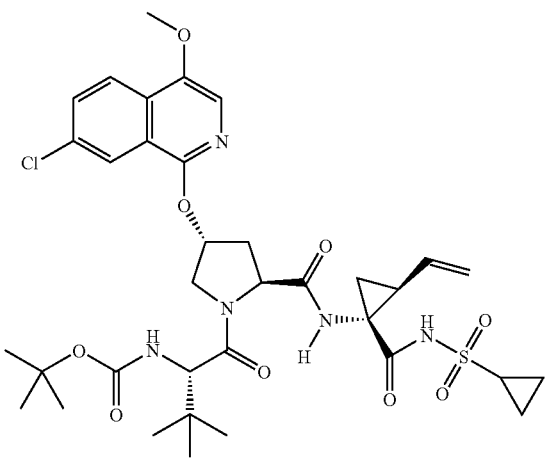

characterized by the following unit cell parameters:

Cell dimensions: a =10.0802 Å b=16.6055 Å c=24.9294 Å

α=90.00 degrees

β=90.00 degrees

γ=90.00 degrees

Space group $P2_12_12_1$

Molecules/unit cell 4 wherein measurement of said crystalline form is at a temperature between about 20° C. to about 25° C.

3. Form H-1 of
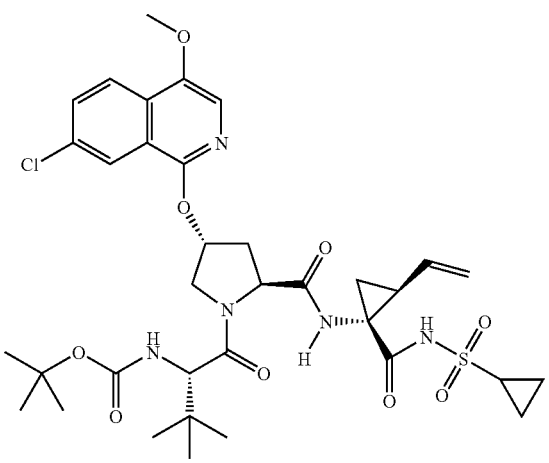
characterized by fractional atomic coordinates within the unit cell of
| Atom | X | Y | Z |
| --- | --- | --- | --- |
| S(1) | 4633(2) | 1649(1) | 6093(1) |
| N(1) | 4351(5) | 2223(2) | 5569(2) |
| N(2) | 3770(4) | 3280(2) | 4728(1) |
| N(3) | 3590(4) | 4937(2) | 5607(2) |
| N(4) | 2677(6) | 4277(4) | 6916(2) |
| O(1) | 3677(8) | 1898(3) | 6465(2) |
| O(2) | 5997(7) | 1682(4) | 6230(3) |
| O(3) | 5891(4) | 1613(2) | 5053(2) |
| O(4) | 5570(3) | 3910(2) | 5093(2) |
| O(5) | 3215(3) | 3701(2) | 5941(1) |
| O(6) | 1838(7) | 5342(6) | 7297(3) |
| O(7) | 965(8) | 4111(6) | 7476(3) |
| C(12) | 3970(6) | 5355(3) | 4730(2) |
| C(13) | 3495(5) | 6077(3) | 5045(2) |
| C(14) | 3637(6) | 5819(3) | 5640(2) |
| C(15) | 3451(5) | 4424(3) | 6021(2) |
| C(16) | 3606(6) | 4702(3) | 6603(2) |
| C(17) | 5104(7) | 4618(4) | 6797(3) |
| C(18) | 5991(7) | 5136(5) | 6512(3) |
| C(19) | 5075(13) | 4835(6) | 7407(3) |
| C(20) | 5573(8) | 3749(5) | 6748(4) |
| C(21) | 1764(11) | 4565(8) | 7247(3) |
| C(26) | 1723(7) | 6568(3) | 4504(2) |
| N(5) | 2626(8) | 6756(3) | 4152(2) |
| C(27) | 2129(14) | 7105(5) | 3682(3) |
| C(28) | 820(19) | 7272(4) | 3590(2) |
| C(29) | −131(13) | 7075(3) | 3984(3) |
| O(8) | 2101(3) | 6221(2) | 4962(2) |
| C(1) | 2870(11 | 464(5) | 5759(4) |
| C(2) | 4303(8) | 668(3) | 5873(3) |
| C(3) | 3535(11 | 137(4) | 6251(3) |
| C(4) | 5005(5) | 2093(3) | 5089(2) |
| C(5) | 4463(4) | 2547(3) | 4620(2) |
| C(6) | 5213(6) | 2451(3) | 4100(3) |
| C(7) | 3892(6) | 2041(3) | 4159(2) |
| C(8) | 3733(7) | 1146(4) | 4208(2) |
| C(9) | 4597(9) | 621(4) | 4048(5) |
| C(10) | 4385(2) | 3907(2) | 4968(2) |
| C(11) | 3500(4) | 4639(2) | 5061(2) |
| C(30) | 304(8) | 6707(3) | 4469(3) |
| C(31) | −584(7) | 6494(3) | 4875(3) |
| C(32) | −1848(7) | 6620(4) | 4807(5) |
| C(33) | −2325(15) | 6965(6) | 4310(7) |
| C(34) | −1576(17) | 7197(5) | 3918(5) |
| Cl(1) | −2988(2) | 6335(2) | 5319(2) |
| C(4') | −530(14) | 5479(13) | 7544(9) |
| C(3') | 1250(30) | 6541(9) | 7751(10) |
| C(2') | 1088(19) | 5236(10) | 8267(5) |
| C(1') | 921(17) | 5659(9) | 7735(6) |
| O(28) | 253(10) | 7631(5) | 3159(3) |
| C(281 | 1165(18) | 7762(10) | 2753(6) |
| OW | 1760(70) | 6690(30) | 6150(30). |
4. Form H-1 of
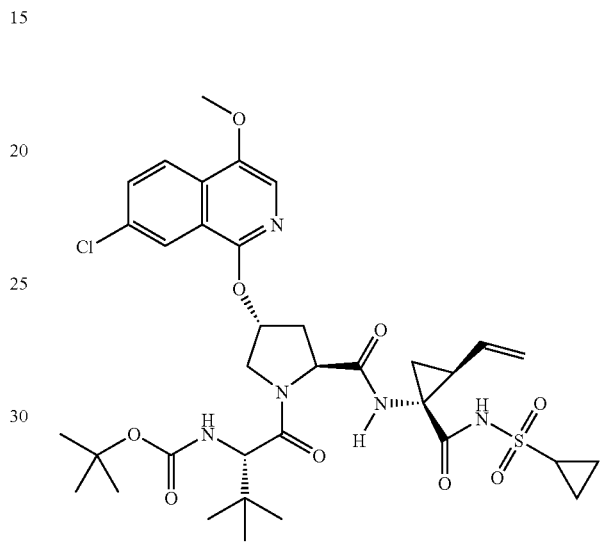
with characteristic peaks in the powder X-Ray diffraction pattern at values of two theta of 6.3±0.1, 7.1±0.1, 9.4±0.1, 10.3±0.1, 12.7±0.1, 13.8±0.1, 17.5±0.1, 18.7±0.1, 20.6±0.1, and 22.5±0.1 at a temperature between about 20° C. and about 25° C.
5. Form H-1 of
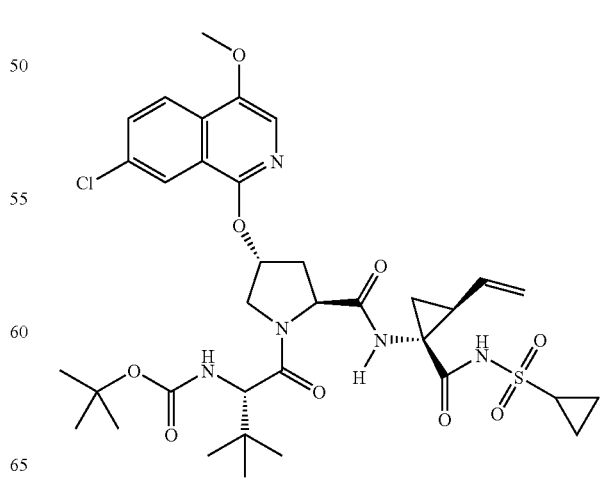

characterized by one or more of the following:

a) a unit cell with parameters substantially equal to the following:

Cell dimensions: a=10.0802 Å
b=16.6055 Å
c=24.9294 Å
α=90.00 degrees
β=90.00 degrees
γ=90.00 degrees
Space group $P2_12_12_1$
Molecules/unit cell 1 wherein measurement of said crystalline form is at a temperature between about 20° C. to about 25° C.;

b) characteristic peaks in the powder X-Ray diffraction pattern at values of two theta of 6.3±0.1, 7.1±0.1, 9.4±0.1, 10.3±0.1, 12.7±0.1, 13.8±0.1, 17.5±0.1, 18.7±0.1, 20.6±0.1, and 22.5±0.1 at a temperature between about 20° C. and about 25° C.; and/or c) characterized by fractional atomic coordinates within the unit cell as listed in Table 3.

6. A pharmaceutical composition comprising Form H-1, with characteristic peaks in the powder X-Ray diffraction pattern at values of two theta of 6.3+0.1, 7.1+0.1, 9.4+0.1, 10.3+0.1, 12.7+0.1, 13.8+0.1, 17.5+0.1, 18.7+0.1, 20.6+0.1, and 22.5+0.1 at a temperature between about 20° C. and about 25° C., of

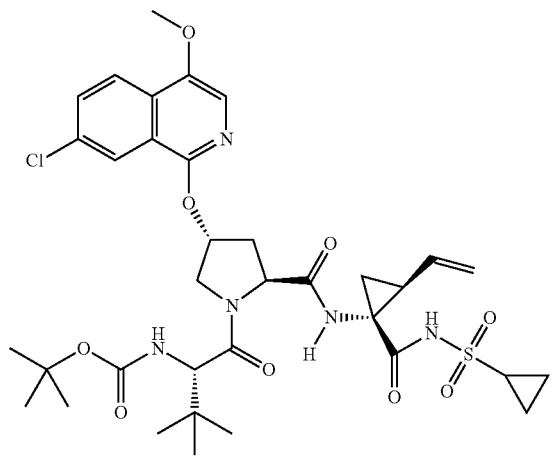

and a pharmaceutically acceptable carrier or diluent.

7. A pharmaceutical composition comprising Form H-1, with characteristic peaks in the powder X-Ray diffraction pattern at values of two theta of 6.3+0.1, 7.1+0.1, 9.4+0.1, 10.3+0.1, 12.7+0.1, 13.8+0.1, 17.5+0.1, 18.7+0.1, 20.6+0.1, and 22.5+0.1 at a temperature between about 20° C. and about 25° C., of

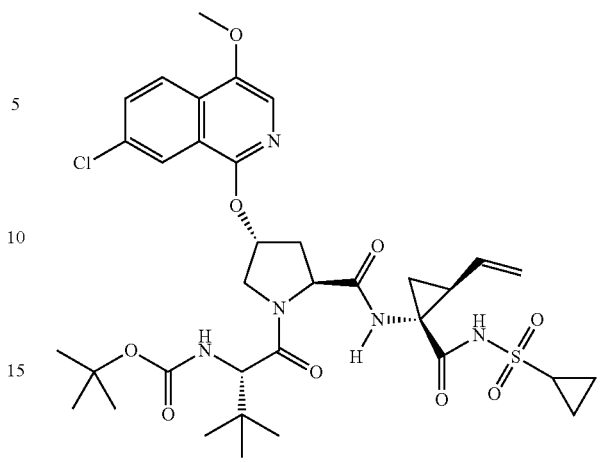

in combination with at least one additional compound having anti-HCV activity.

8. The composition of claim 7 wherein at least one of the additional compounds having anti-HCV activity is an interferon or ribavirin.

9. The composition of claim 8 wherein the interferon is selected from interferon alpha 2B, pegylated interferon alpha, consensus interferon, interferon alpha 2A, and lymphoblastiod interferon tau.

10. The composition of claim 7 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

11. A method of treating HCV infection in a mammal comprising administering to the mammal a therapeutically-effective amount of Form H-1 of

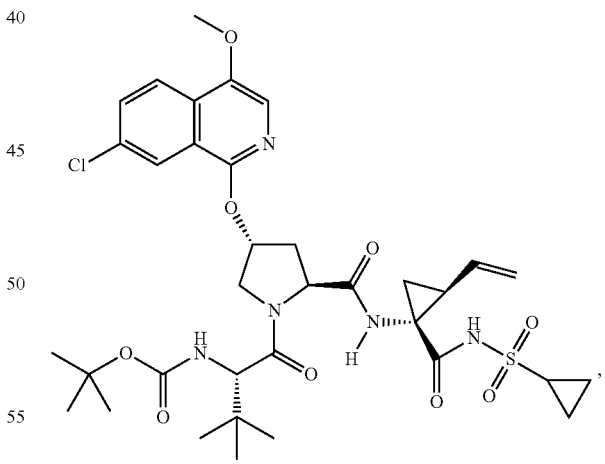

as characterized in claim 4.

12. The method of claim 11 wherein the mammal is a human.

* * * * *

UNITED STATES PATENT AND TRADEMARK OFFICE
CERTIFICATE OF CORRECTION

PATENT NO. : 8,202,996 B2  
APPLICATION NO. : 12/329969  
DATED : June 19, 2012  
INVENTOR(S) : Robert Kevin Perrone et al.

It is certified that error appears in the above-identified patent and that said Letters Patent is hereby corrected as shown below:

In the Specification:

Column 7, line 33, change "lymphoblastiod" to -- lymphoblastoid --.

Column 7, line 66, change "Imiqimod," to -- Imiquimod, --.

Column 7, line 66, change "5'-monophospate" to -- 5'-monophosphate --.

Column 26, line 30, change "2870(11" to -- 2870(11) --.

Column 26, line 32, change "3535(11" to -- 3535(11) --.

Column 26, line 44, change "5075(13" to -- 5075(13) --.

Column 26, line 46, change "1764(11" to -- 1764(11) --.

Column 30, line 60, change "C(281" to -- C(281) --.

In the Claims:

Claim 3:

Column 29, line 44, change "5075(13" to -- 5075(13) --.

Column 29, line 46, change "1764(11" to -- 1764(11) --.

Column 29, line 52, change "2870(11" to -- 2870(11) --.

Column 29, line 54, change "3535(11" to -- 3535(11) --.

Column 30, line 10, change "C(281" to -- C(281) --.

Signed and Sealed this  
Eighth Day of April, 2014

Michelle K. Lee  
*Deputy Director of the United States Patent and Trademark Office*

CERTIFICATE OF CORRECTION (continued)
U.S. Pat. No. 8,202,996 B2

In the Claims:

Claim 5:

Column 31, line 25, below "the unit cell as listed in Table 3", insert

-- Table 3
Atomic coordinates

| Atom | X | Y | Z | Atom | X | Y | Z |
|---|---|---|---|---|---|---|---|
| S(1) | 4633(2) | 1649(1) | 6093(1) | O(8) | 2101(3) | 6221(2) | 4962(2) |
| N(1) | 4351(5) | 2223(2) | 5569(2) | C(1) | 2870(11) | 464(5) | 5759(4) |
| N(2) | 3770(4) | 3280(2) | 4728(1) | C(2) | 4303(8) | 668(3) | 5873(3) |
| N(3) | 3590(4) | 4937(2) | 5607(2) | C(3) | 3535(11) | 137(4) | 6251(3) |
| N(4) | 2677(6) | 4277(4) | 6916(2) | C(4) | 5005(5) | 2093(3) | 5089(2) |
| O(1) | 3677(8) | 1898(3) | 6465(2) | C(5) | 4463(4) | 2547(3) | 4620(2) |
| O(2) | 5997(7) | 1682(4) | 6230(3) | C(6) | 5213(6) | 2451(3) | 4100(2) |
| O(3) | 5891(4) | 1613(2) | 5053(2) | C(7) | 3892(6) | 2041(3) | 4159(2) |
| O(4) | 5570(3) | 3910(2) | 5093(2) | C(8) | 3733(7) | 1146(4) | 4208(2) |
| O(5) | 3215(3) | 3701(2) | 5941(1) | C(9) | 4597(9) | 621(4) | 4048(5) |
| O(6) | 1838(7) | 5342(6) | 7297(3) | C(10) | 4385(4) | 3907(2) | 4968(2) |
| O(7) | 965(8) | 4111(6) | 7476(3) | C(11) | 3500(4) | 4639(2) | 5061(2) |
| C(12) | 3970(6) | 5355(3) | 4730(2) | C(30) | 304(8) | 6707(3) | 4469(3) |
| C(13) | 3495(5) | 6077(3) | 5045(2) | C(31) | -584(7) | 6494(3) | 4875(3) |
| C(14) | 3637(6) | 5819(3) | 5640(2) | C(32) | -1848(7) | 6620(4) | 4807(5) |
| C(15) | 3451(5) | 4424(3) | 6021(2) | C(33) | -2325(15) | 6965(6) | 4310(7) |
| C(16) | 3606(6) | 4702(3) | 6603(2) | C(34) | -1576(17) | 7197(5) | 3918(5) |
| C(17) | 5104(7) | 4618(4) | 6797(3) | Cl(1) | -2988(2) | 6335(2) | 5319(2) |
| C(18) | 5991(7) | 5136(5) | 6512(3) | C(4') | -530(14) | 5479(13) | 7544(9) |
| C(19) | 5075(13) | 4835(6) | 7407(3) | C(3') | 1250(30) | 6541(9) | 7751(10) |
| C(20) | 5573(8) | 3749(5) | 6748(4) | C(2') | 1088(19) | 5236(10) | 8267(5) |
| C(21) | 1764(11) | 4565(8) | 7247(3) | C(1') | 921(17) | 5659(9) | 7735(6) |
| C(26) | 1723(7) | 6568(3) | 4504(2) | O(28) | 253(10) | 7631(5) | 3159(3) |
| N(5) | 2626(8) | 6756(3) | 4152(2) | C(281) | 1165(18) | 7762(10) | 2753(6) |
| C(27) | 2129(14) | 7105(5) | 3682(3) | OW | 1760(70) | 6690(30) | 6150(30) |
| C(28) | 820(19) | 7272(4) | 3590(3) | | | | |
| C(29) | -131(13) | 7075(3) | 3984(3) | | | | |

--.

Claim 9:

Column 32, lines 27 and 28, change "lymphoblastiod" to -- lymphoblastoid --.

Claim 10:

Column 32, line 33, change "Imiqimod," to -- Imiquimod, --.

Column 32, lines 33 and 34, change "5'-monophospate" to -- 5'-monophosphate --.